US006177572B1

(12) United States Patent
Wang

(10) Patent No.: US 6,177,572 B1
(45) Date of Patent: *Jan. 23, 2001

(54) SOLID AND LIQUID-PHASE SYNTHESIS OF BENZOXAZOLES AND BENZOTHIAZOLES AND THEIR USE

(75) Inventor: Fengjiang Wang, Northborough, MA (US)

(73) Assignee: Sepracor, Inc., Marlborough, MA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/915,261

(22) Filed: Aug. 20, 1997

(51) Int. Cl.[7] ..................... C07D 263/54; C07D 277/62; A61K 31/423; A61K 31/428
(52) U.S. Cl. .................... 548/152; 548/171; 548/217; 548/224; 514/367; 514/375
(58) Field of Search ................................. 548/152, 171, 548/217, 224; 514/367, 375

(56) References Cited

U.S. PATENT DOCUMENTS

| | | | |
|---|---|---|---|
| 1,745,843 | 2/1930 | Clarke | 548/217 |
| 5,164,371 | 11/1992 | Edwards et al. | 514/18 |
| 5,169,952 | 12/1992 | Askin et al. | 544/137 |
| 5,482,962 | * 1/1996 | Hormann | 514/415 |
| 5,565,324 | 10/1996 | Still et al. | 435/6 |

FOREIGN PATENT DOCUMENTS

| | | | |
|---|---|---|---|
| 2327096 | * 12/1974 | (DE) | 548/224 |
| 53-43507 | 7/1970 | (JP) . | |

OTHER PUBLICATIONS

M. R. Brann, et al., "Cell–Based Assays for G–Protein–Coupled/Tyrosine Kinase–Coupled Receptors," *Journal of Biomolecular Screening*, 1(1):43–45 (1996).*
M.O. Chaney et al., "The Structure of A23187, a Divalent Cation Ionophore," *Journal of the American Chemical Society*, 96(6): 1932–1933, (1974).*
J. Coste, et al., "PyBOP®: A New Peptide Coupling Reagent Devoid of Toxic By–Product," *Tetrahedron Lett.*, 31:205–208, (1990).*
L. David et al., "Production by Controlled Biosynthesis of a Novel Ionophore Antibiotic, Cezomycin (Demethylamino A23187)," *Journal of Antibiotics*, 35: 1409–1411 (1982).*
S. Hobbs DeWitt, et al., "Diversomers": An Approach to Nonpeptide, Nonoligomeric Chemical Diversity *Proc. Natl. Acad. Sci.* USA, 90:6909–6913 (1983).*
D. W. Dunwell, et al., "2–Aryl–5–Benzoxazolealkanoic Acid Derivatives with Notable Antiinflammatory Activity", *J. Med. Chem.*, 18:53–58 (1975).*
D. W. Dunwell and Delme Evans, "Synthesis and Antiinflammatory Activity of Some 2–Aryl–6–benzoxazoleacetic Acid Derivatives", *J. Med. Chem.*, 20(6):797–801 (1977).*
D. W. Dunwell, et al. "Synthesis and Antiinflammatory Activity of Some 2–Heteroaryl–α–methyl–5–benzoxazoleacetic Acids", *J. Med. Chem.*, 18(11): 1158–1159 (1975).*

(List continued on next page.)

*Primary Examiner*—Floyd D. Higel
(74) *Attorney, Agent, or Firm*—Matthew P. Vincent; Dana M. Gordon; Foley, Hoag & Eliot LLP

(57) ABSTRACT

Methods for preparing benzoxazoles and benzothiazoles on solid supports. Substituted benzothiazoles and benzoxazoles, libraries of the compounds, and methods of using the compounds are also disclosed.

22 Claims, 4 Drawing Sheets

OTHER PUBLICATIONS

D.J. Ecker, et al., "Combinatorial Drug Discovery: Which Methods Will Produce the Greatest Value?" *Biotechnology*, 13: 351–360 (1995).*

P.D. Edwards, et al., "Peptidyl 2–α–Ketoheterocyclic Inhibitors of Human Neutrophil Elastase. 3. In Vitro and in Vivo Potency of a Series of Peptidyl α–Ketobenzoxazoles", *J. Med. Chem.*, 38:3972–3982 (1995).*

P.D. Edwards, et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.*, 114: 1854–1863 (1992).*

D. Evans, et al., "Synthesis and Antiinflammatory Activity of Some 2–Substituted 4– and 7–Benzoxazoleacetic and α–Methylacetic Acids", *J. Med. Chem.*, 20(1):169–171 (1977).*

F. Forman and I. Sucholeiki, "Solid–Phase Synthesis of Biaryls via the Stille Reaction," *J. Org. Chem.*, 60(3): 523–528 (1995).*

M. A. Gallop, et al., "Applications of Combinatorial Technologies to Drug Discovery. 1. Background and Peptide Combinatorial Libraries," *J. Med. Chem.*, 37(9): 1233–1251 (1994).*

D. A. Goff and R. N. Zuckermann, "Solid–Phase Synthesis of Defined 1,4–Benzodiazepine–2,5–dione Mixtures", *J. Org. Chem.*, 60:5744–5745 (1995).*

S.W. Goldstein and P. J. Dambek, "A Facile Synthesis of Methyl 2–Substituted–4–benzoxazlecarboxylates," *J. Heterocyclic Chem.*, 27: 335–336 (1990).*

E.M. Gordon, et al., "Applications of Combinatorial Technologies to Drug Discovery. 2. Combinatorial Organic Synthesis, Library Screening Strategies, and Future Directions." *J. Med. Chem.* 37(10):1385–1401 (1994).*

R.D. Haugwitz, et al., "Antiparasitic Agents. 3. Synthesis and Anthelmintic Activities of Novel 2–Pyridinyl–5–isothiocyanatobenzimidazoles," *J. Med. Chem.*, 22(9):1113–1118 (1979).*

R.D Haugwitz, et al., "Antiparasitic Agents. 5. Synthesis and Anthelmintic Activities of Novel 2–Heteroaromatic–Substituted Isothiocyanatobenzoxaoles and Benzothiazoles," *J. Med Chem.* 25(8):969–974 (1982).*

J.R. Hauske and P. Dorff "A Solid Phase CBZ Chloride Equivalent–A New Matrix Specific Linker", *Tetrahedron Lett.*, 35(10: 1589–1592 (1995).*

P.H.H. Hermkens, et al., "Solid–Phase Organic Reactions: A Review of the Recent Literature," *Tetrahedron*, 52(13):4527–4554 (1996).*

M. Hiroshige, et al., "Palladium–Mediated Macrocyclization of Solid Support and Its Applications to Cominatorial Synthesis," *J. Am. Chem. Soc.*, 117(46):11590–11591(1995).*

C.P. Holmes et al., "Reagents for Combinatorial Organic Synthesis: Development of a New 0–Nitrobenzyl Photolabile Linker for Solid Phase Synthesis" *J. Org. Chem.*, 60: 2318–2319 (1995).*

C.P. Holmes et al., "Strategies for Combinatorial Organic Synthesis: Solution and Polymer–Supported Synthesis of 4–Thiazolidinones and 4–Methathazanones Derived from Amino Acids," *J. Org. Chem.*, 60(22): 7328–7333(1995).*

R.A. Houghten, et al., "Generation and use of synthetic peptide combinatorial libraries for basic research and drug discovery," *Nature*, 354:84–86 (1991).*

T. Kusumi et al., "Structure of the Novel Antibiotics Boxazomycins A, B, and C", *J. Am. Chem. Soc.*, 110(9):2954–2958 (1988).*

Y. Katsura, et al., "Studies on Antiulcer Drugs. II. Synthesis and Antiulcer Activities of Imidazo[1,2–α] pyridinyl–2–alklaminobenzoxazoles and 5,6,7,8–Tetrahydroimidazo[1,2–α]pyridinyl Derivatives" *Chem. Pharm. Bull.*, 40(2):371–380 (1992).*

Y. Katsura, et al., "Studies on Antiulcer Drugs. III. Synthesis and Antiulcer Activities of Imidazo[1,2–α]pyridinylethylbenzoxazoles and Related Compounds. A Novel Class of Histamine $H_2$–Receptor Antagonists," *Chem. Pharm. Bull.*, 40(6):1424–1438 (1992).*

E.K. Kick et al. "Expedient Method for the Solid–Phase Synthesis of Aspartic Acid Protease Inhibitors Directed toward the Generation of Libraries," *J. Med. Chem.*, 38:1427–1430 (1995).*

M. J. Kurth et al., "Library–Based Lead Compound Discovery: Antioxidants by an Analogous Synthesis/ Deconvolutive Assay Stategy," *J. Org Chem.*, 59: 5862–5864, (1994).*

T.L. Messier, et al., "High Throughput Asays of Cloned Adrenergic, Muscarinic, Neurokinin, and Neurotrophin Receptors in Living Mammalian Cells," *J. Pharmacol. and Toxicol.*, 76: 308–311 (1995).*

W.H. Moos and G.D. Green, "Recent Advances in the Generation of Molecular Diversity", *Annual Rpts in Medicinal Chem.*, Bristol, JA., Ed.; Academic Press, Inc.; San Diego, CA, 28: 315–324 (1993).*

J.J. Nestor, et al. Synthesis of a Novel Class of Heteroaromatic Amino Acids and Their Use in the*

A. Orjales, et al., "Synthesis and Structure–Activity Relationship of New Piperidinyl and Piperazinyl Derivatives as Antiallergics", *J. Heterocyclic Chem.*, 32: 707–718 (1995).*

M.J. Plunkett and J. A. Ellman, "A Silicon–Based Linker for Traceless Solid–Phase Synthesis," *J. Org. Chem.*, 60:6006–6007 (1995).*

D.B. Pritchett et al., "Structure and Functional expression of cloned rat serotonin 5HT–2 receptor," *EMBOJ.*, 7:4135–4140 (1988).*

J.G. Stack et al., "A New Chiral Auxiliary for Asymmetric Thermal Reactions: High Stereocontrol in Radical Addition, Allylation, and Annulation Reactions," *J. Am. Chem. Soc.*, 114: 7007–7018 (1992).*

M. J. Suto and William R. Turner, "Synthesis of Boxazomycin B and Related Analogs," *Tetrahedron Lett*, 36: 7213–7216 (1995).*

N.K. Terrett et al., "Combinatorial Synthesis—The Design of Compound Libraries and their Application to Drug Discovery", *Tetrahedron*, 51:8135–8173 (1995).*

L. Thompson and J. Ellman, "Synthesis and Applications of Small Molecule Libraries," *Chem. Rev.*, 96: 555–600 (1996).*

C. Veale et al., "Non–Peptidic Inhibitors of Human Leukocyte Elastase. 4. Design, Synthesis, and in Vitro and in Vivo Activity for a Series of β–Carbolinone–Containing Trifluoromethyl Ketones," *J. Med. Chem.*, 38: 86–97 (1995).*

J. W. Westley et al. "Isolation and Characterization of Novel Polyether Antibiotic of Pyrrolether Class Antibiotic X–14885A," *J. Antibiotoc.,*.10: 1275–1278 (1983).*

P. Wipf and A. Cunningham, "A Solid Phase Protocol of the Biginelli Dihydropyrimidine Synthesis Suitable for Combinatorial Chemistry", *Tetrahedron Lett.*, 36(43): 7819–7822 (1995).*

* cited by examiner

SOLID AND LIQUID-PHASE SYNTHESIS OF BENZOXAZOLES AND BENZOTHIAZOLES AND THEIR USE

BACKGROUND OF THE INVENTION

The synthesis and screening of small molecule combinatorial libraries has become an important new technology for drug discovery. (For reviews see: (a) Gallop, M. A.; Barrett, R. W.; Dower, W. J.; Fodor, S. P. A.; Gordon, E. M. *J. Med. Chem.* 1994, 37, 1233. (b) Gordon, E. M.; Barrett, R. W.; Dower, W. J.; Fodor, S. P. A.; Gallop, M. A. *J. Med. Chem.* 1994, 37, 1385. (c) Moos, W. H.; Green, G. D.; Pavia, M. R. Recent Advances in Generation of Molecular Diversity. in *Annual Reports in Medicinal Chemistry;* Bristol, J. A., Ed.; Academic Press, Inc.; San Diego, Calif., 1993; Vol. 28, pp. 315–324. (d) Ecker, D. J.; Crooke, S. T. *Biotechnology* 1995, 13, 351. (e) Terrett, N. K.; Gardner, M.; Gordon, D. W.; Kobylecki, R. J.; Steele J. Tetrahedron 1995, 51, 8135. (f) Thompson, L. A.; Ellman, J. A. Chem. Rev. 1996, 96, 555. (g) Herkens, P. H. H.; Ottenheijm, H. C. J.; Rees, D. *Tetrahedron,* 1996, 52, 4527. (h) Fruchtel, J. S.; Jung, G. *Angew. Chem. Int. Ed. Engl.* 1996, 35, 17.) A convenient format for the generation of these libraries is synthesis of organic compounds on a solid phase. Solid phase synthesis is especially useful for reactions where excess reagents can be used to drive the reactions to completion. The excess reagents and soluble byproducts can be easily removed. (See, for example: (a) Kurth, M. J.; Randall, L. A. A.; Chen, C.; Melander, C.; Miller, R. B. *J. Org. Chem.* 1994, 59, 5862. (b) Hiroshige, M.; Hauske, J. R.; Zhou, P. *J. Am. Chem. Soc.* 1995,117,11590. (c) Wipf, P.; Cunningham, A. *Tetrahedron Lett.* 1995, 36, 7819. (d) Goff, D. A.; Zuckermann, R. N. *J. Org. Chem.* 1995, 60, 5744. (e) Plunkett, M. J.; Ellman, J. A. *J. Org. Chem.* 1995, 60, 6006. (f) Kick, E. K.; Ellman, J. A. *J. Med. Chem.* 1995, 38, 1427. (g) Forman, F. W.; Sucholeiki, I. *J. Org. Chem.* 1995, 60, 523. (h) Holmes, C. P.; Jones, D. G. *J. Org. Chem.* 1995, 60, 2318. (i) Holmes, C. P.; Chinn, J. P.; Look, G. C.; Gordon, E. M.; Gallop, M. A. *J. Org. Chem.* 1995, 60, 7328.) Another important feature of solid phase synthesis is allowing "split and combine" methodology to be employed for library construction. Thus, generating diverse combinatorial libraries requires the development of solid phase syntheses of biologically active molecules on solid support, and the exploration of such synthetic methodologies for preparation of libraries.

Often compounds isolated from natural products have biological activity. For example, benzoxazole containing compounds, isolated from natural products or synthesized, have remarkable biological activities. (See: Boyd, G. V. In *Comprehensive Heterocyclic Chemistry,* Vol. 6; Part 4B, Katritzky, A. R.; Rees, C. W., Eds.; Pergammon: Oxford, 1984; p178.) The boxazomycins A, B, and C, isolated from a soil sample in Taiwan, are gram-positive antibacterial agents containing the benzoxazole ring system. (See: (a) Kusumi, T.; Ooi, T; Walchi, M. R.; Kakisawa, H. *J. Am. Chem. Soc.* 1988, 110, 2954. (b) Suto, M. J.; Turner, W. R. *Tetrahedron Lett.* 1995, 36, 7213.) The 4-carboxybenzoxazole ring system is found in nature in number of polycyclic antibiotics, such as X-14885A, Calcimycin and Cezomycin. (See: (a) Chaney, M. O.; Demarco, P. V.; Jones, N. D.; Occolowitz, J. L. *J. Am. Chem. Soc.* 1974, 96, 1932. (b) David, L.; Dergomard, A. *J. Antibiotic.* 1982, 35, 1409. (c) Westly, J. W.; Liu, J. W.; Blount, J. F.; Sello, L. H.; Troupe, N.; Miller, P. A.. *J. Antibiotic.* 1983, 36, 1275.) A variety of 2-substituted benzoxazoles have been claimed to possess antiparasitic activity against *Turbatrix aceti, Syphacia obvelata, Nippostronglyus brasiliensis, helminths, Eimeria tenella* and *Eimeria necatrix,* and *S. obvelata* and *Aspicularis tetraptera.* (See: (a) Haugwitz, R. D.; Maurer, B. V.; Jacobs, G. A.; Narayanan, V. L.; Cruthers, L. R.; Szanto, J. *J. Med. Chem.* 1979, 22, 1113. (b) Haugwitz, R. D.; Angel, R. G.; Jacobs, G. A; Maurer, B. V.; Narayanan, V. L.; Cruthers; Szanto, J. *J. Med. Chem.* 1982, 25, 969.) Evans and co-workers synthesized 2-aryl-6-benzoxazoleacetic acid derivatives and screened the compounds for anti inflammatory activity on the carrageenan-induced rat paw edema test. (See: (a) Dunwell, D. W. ; Evans, D.; Hicks, T. A.; Cashin, C. H.; Kitchen, A. *J. Med. Chem.* 1975, 18, 53. (b) Dunwell, D. W.; Evans, D.; Hicks, T. A. J. Med. Chem. 1975, 18, 1158. (c) Evans, D.; Smith, C. E.; Williamson, W. R. N. *J. Med. Chem.* 1977, 20, 169. (d) Dunwell, D. W.; Evans, D. J. Med. Chem. 1977, 20, 797.) Recently, a series of peptidyl-ketobenzoxazoles were synthesized and evaluated for their in vitro and in vivo inhibition of human neutrophil elastase. (See: (a) Edwards, P. D.; Meyer, E. F.; Vijahalakshmi, J.; Tuthill, P.A.; Andisik, D. A.; Gomes, B.; Strimpler, A. *J. Am. Chem. Soc.* 1992, 114, 1854. (b) Edwards, P. D.; Damewood, J. R.; Steelman, G. B.; Bryant, C.; Gomes, B.; Williams, J. *J. Med. Chem.* 1995, 38, 87. (c) Edwards, P. D.; Zottola, M. A.; Davis, M.; Williams, J.; Tuthill, P.A. *J. Med. Chem.* 1995, 38, 3972.) A Japanese group reported that imidazo[1,2--]pyridinylbenzoxazoles exhibited antiulcer activity in the anti-stress ulcer screen in rats. (See: (a) Katsura, Y.; Nishino, S.; Inoue, Y.; Tomoi, M.; Takasugi, H. *Chem. Pharm. Bull.* 1992, 40, 371. (b) Katsura, Y.; Nishino, S.; Inoue, Y.; Tomoi, M.; Itoh, H. Takasugi, H. *Chem. Pharm. Bull.* 1992, 40, 1424.)

Preparation of heterocyclic containing compounds, such as, for example, benzoxazoles, can be synthetically challenging. Often multiple synthetic steps are required to prepare the desired heterocyclic compound. As a consequence of multistep syntheses, reaction conditions utilized to form heterocyclic compounds such as benzoxazoles and benzothiazoles can facilitate degradation of the remaining molecular functionality. Additionally, synthetic manipulation of a molecule which contains a benzoxazole, for example, can cause degradation of the benzoxazole portion of the molecule.

SUMMARY OF THE INVENTION

The invention relates to heterocyclic containing compounds, such as benzoxazoles and benzothiazoles, libraries of these compounds, and methods of preparing and using the compounds.

In one aspect, the invention provides methods for preparing a benzoxazole or a benzothiazole via solid phase synthesis. The method includes the step of treating a 2-amidophenol or a 2-amidothiophenol with a cyclization-dehydration agent under suitable conditions, wherein the 2-amidophenol or 2-amidothiophenol is coupled to a solid phase support through a linker group, such that a benzoxazole or a benzothiazole is formed.

In another aspect, the invention provides methods for preparing a compound represented by the formula (Formula I):

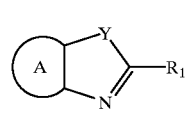

(I)

A is a substituted or unsubstituted aryl or heteroaryl group and Y is O or S. $R_1$ is a linear or branched, substituted or unsubstituted alkyl group, a substituted or unsubstituted aryl group, or a linker group attached to a solid support, or a salt thereof. The method includes reacting a compound having the formula (Formula

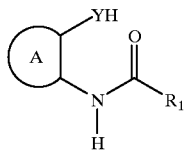

wherein Y is O or S, with a cyclization-dehydration reagent under suitable conditions such that a compound of Formula I is formed.

In yet another aspect, the invention provides methods of preparing a compound represented by the formula (Formula III):

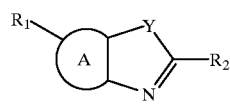

A is a substituted or unsubstituted aryl or heteroaryl group and Y is O or S. $R_1$ is a linear or branched, substituted or unsubstituted alkyl group, a substituted or unsubstituted aryl group, or a linker group attached to a solid support. $R_2$ is a linear or branched, substituted or unsubstituted alkyl group, a substituted or unsubstituted aryl group, or a salt thereof. The method includes reacting a compound having the formula (Formula IV)

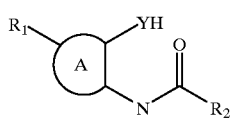

wherein Y is O or S, with a cyclization-dehydration reagent under suitable conditions such that a compound of Formula III is formed.

In yet another aspect, the invention provides methods for preparing a library including benzoxazoles, benzothiazoles or both via solid phase synthesis. The method includes treating a plurality of 2-amidophenols, 2-amidothiophenols, or mixtures thereof with a cyclization-dehydration agent under suitable conditions, wherein each of the 2-amidophenols or 2-amidothiophenols is independently coupled to a solid phase support through a linker group, such that benzoxazoles or benzothiazoles are formed.

In still yet another aspect, the invention provides methods for preparing a library of compounds represented by the formula (Formula I):

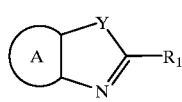

A is a substituted or unsubstituted aryl or heteroaryl group and Y is O or S. $R_1$ is a linear or branched, substituted or unsubstituted alkyl group, a substituted or unsubstituted aryl group, or a linker group attached to a solid support, or a salt thereof. The method includes the step of reacting a plurality of compounds having the formula (Formula II):

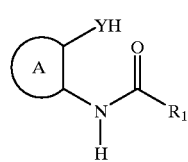

wherein Y is O or S, with a cyclization-dehydration reagent under suitable conditions such that a library of compounds of Formula I is formed.

In another aspect, the invention provides methods of preparing a library of compounds represented by the formula (Formula III):

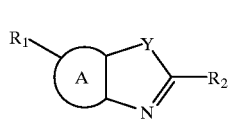

A is a substituted or unsubstituted aryl or heteroaryl group and Y is O or S. $R_1$ is a linear or branched, substituted or unsubstituted alkyl group, a substituted or unsubstituted aryl group, or a linker group attached to a solid support. $R_2$ is a linear or branched, substituted or unsubstituted alkyl group, a substituted or unsubstituted aryl group, or a salt thereof. The method includes the step of reacting a plurality of compounds having the formula (Formula IV)

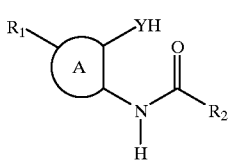

wherein Y is O or S, with a cyclization-dehydration reagent under suitable conditions such that a library of compounds of Formula III is formed.

In still another aspect, the invention provides compounds represented by the formula (Formula V):

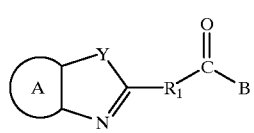

and salts thereof. A is a substituted or unsubstituted aryl group and Y is O or S. $R_1$ is a substituted or unsubstituted moiety that is bonded at least to a benzoxazole or benzothiazole group and the group

More specifically, $R_1$ is a linear or branched alkyl group, an alkenyl group, an alkoxyalkyl group, a thioalkoxyalkyl group, or an aryl group. B is —N(R$_2$)R$_3$N(R$_4$) (R$_5$), wherein R$_2$ is a hydrogen atom, R$_3$ is a linear or branched, substituted or unsubstituted alkyl diradical and R$_4$ and R$_5$ are each independently a hydrogen atom, a linker group attached to a solid support, or R$_2$ and R$_4$ taken together represent a substituted or unsubstituted cycloalkyl group.

In another aspect, the invention provides compounds presented by the formula (Formula VI):

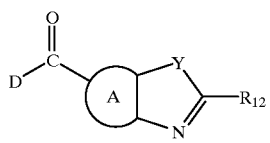
(VI)

and salts thereof. A is an aryl group and Y is O or S. D is

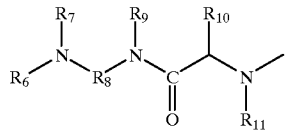

R$_6$ and R$_7$ are each independently a hydrogen atom or a linker group to a solid support. R$_8$ is a substituted or unsubstituted moiety that is bonded at least to NR R$^7$ and NR$_9$. More specifically, R$_8$ is a linear or branched alkyl group, an alkoxyalkyl group, or an aryl group. R$_9$ is a hydrogen atom or R$_7$ and R$_9$ when taken together represent a cycloalkyl group. R$_{10}$ is a linear or branched, substituted or unsubstituted alkyl group or substituted or unsubstituted aryl group. R$_{11}$ is a hydrogen atom and R$_{12}$ is a linear or branched, substituted or unsubstituted alkyl group, a linear or branched, substituted or unsubstituted alkenyl group,or a substituted or unsubstituted aryl group.

In still another aspect, the invention provides a library of compounds represented by the formula (Formula V):

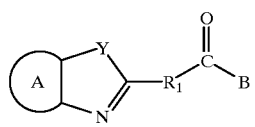
(V)

and salts thereof. A is a substituted or unsubstituted aryl group and Y is O or S. R$_1$ is a substituted or unsubstituted moiety that is bonded at least to a benzoxazole or benzothiazole group and the group (C↑O)B. More specifically, R$_1$ is a linear or branched alkyl group, an alkenyl group, an alkoxyalkyl group, a thioalkoxyalkyl group, or an aryl group. B is —N(R$_2$)R$_3$N(R$_4$) (R$_5$), wherein R$_2$ is a hydrogen atom and R$_3$ is a linear or branched, substituted or unsubstituted alkyl diradical. R$_4$ and R$_5$ are each independently a hydrogen atom, a linker group to a solid support, or R$_2$ and R$_4$ taken together represent a substituted or unsubstituted cycloalkyl group.

In another aspect, the invention provides a library of compounds represented by the formula (Formula VI):

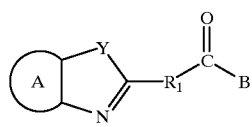
(V)

and salts thereof. A is an aryl group and Y is O or S. D is

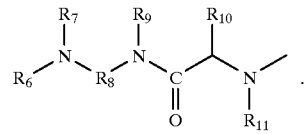

R$_6$ and R$_7$ are each independently a hydrogen atom or a linker group to a solid support. R$_8$ is a substituted or unsubstituted moiety that is bonded at least to NR$^7$R$^6$ and NR$^9$. More specifically, R$_8$ is a linear or branched alkyl group, an alkoxyalkyl group, or an aryl group. R$_9$ is a hydrogen atom or R$_7$ and Rgwhen taken together represent an cycloalkyl group. R$_{10}$ is a linear or branched, substituted or unsubstituted alkyl group or a substituted or unsubstituted aryl group. substituted or unsubstituted R$_{11}$ is a hydrogen atom and R$_{12}$ is a linear or branched, substituted or unsubstituted alkyl group, a linear or branched, substituted or unsubstituted alkenyl group, or a substituted or unsubstituted aryl group.

In yet another aspect, the invention provides pharmaceutical compositions comprising an effective amount of a compound represented by the formula (Formula V):

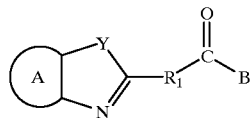
(V)

and salts thereof. A is a substituted or unsubstituted aryl group and Y is O or S. R$_1$ is a substituted or unsubstituted moiety that is bonded at least to a benzoxazole or benzothiazole group and the group (C↑O)B. More specifically, R$_1$ is a linear or branched alkyl group, an alkenyl group, an alkoxyalkyl group, a thioalkoxyalkyl group, or an aryl group. B is —N(R$_2$)R$_3$N(R$_4$) (R$_5$), wherein R$_2$ is a hydrogen atom and R$_3$ is a linear or branched, substituted or unsubstituted alkyl diradical. R$_4$ and R$_5$ are each independently a hydrogen atom, a linker group attached to a solid support, or R$_2$ and R$_4$ taken together represent a substituted or unsubstituted cycloalkyl group.

In still another aspect, the invention provides pharmaceutical compositions comprising an effective amount of 35 a compound represented by the formula (Formula VI):

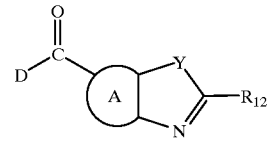
(VI)

and salts thereof. A is an aryl group and is O or S. D is

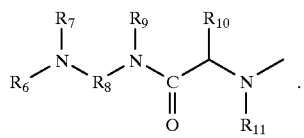

$R_6$ and $R_7$ are each independently a hydrogen atom or a linker group attached to a solid support. $R_8$ is a substituted or unsubstituted moiety that is bonded at least to $NR^6R^7$ and $NR^9$. More specifically, $R_8$ is a linear or branched alkyl group, an alkoxyalkyl group, or an aryl group. $R_9$ is a hydrogen atom or $R_7$ and $R_9$ when taken together represent a cycloalkyl group. $R_{10}$ is a linear or branched, substituted or unsubstituted alkyl group or a substituted or unsubstituted aryl group. $R_{11}$ is a hydrogen atom and $R_{12}$ is a linear or branched, substituted or unsubstituted alkyl group, a linear or branched, substituted or unsubstituted alkenyl group, or a substituted or unsubstituted aryl group.

DETAILED DESCRIPTION OF THE INVENTION

Figure 1:
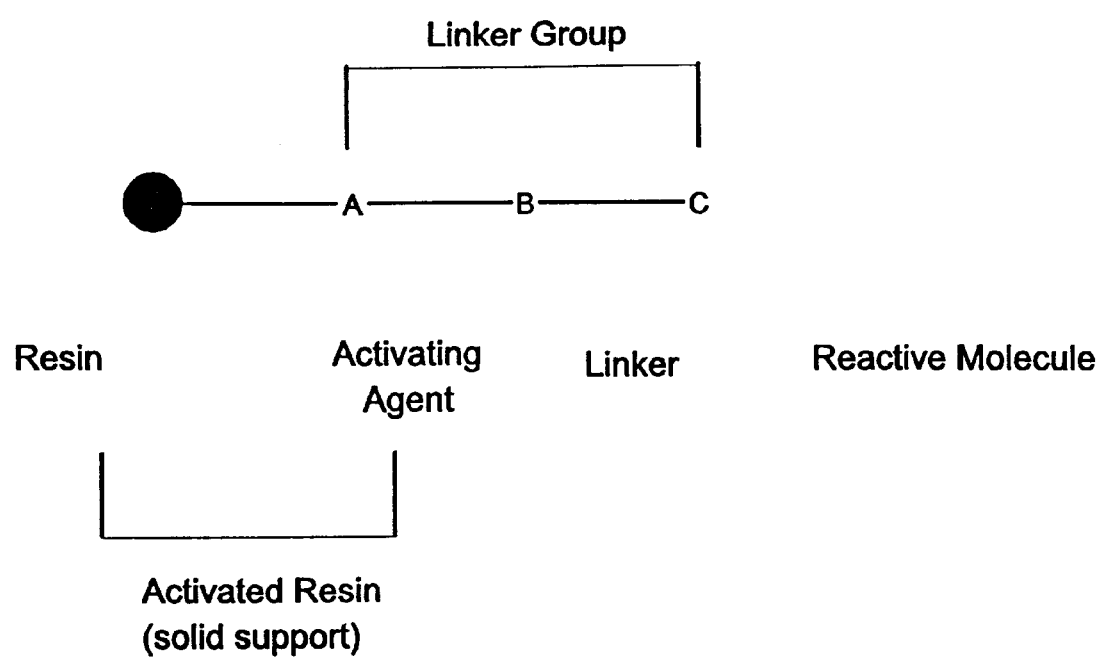
FIG. 1 depicts the portions of a polymer supported linker group.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise stated.

The invention relates to heterocyclic containing compounds, such as benzoxazoles and benzothiazoles, libraries of these compounds, and methods of preparing and using the compounds.

Applying solid-phase synthesis techniques to cyclization-dehydration of, for example, amino-phenols to prepare a benzoxazole, effectively isolates the resultant benzoxazole on the resin, preventing unwanted side reactions. In addition, a solid-phase methodology can be conveniently incorporated into combinatorial library strategies for producing an array of highly functionalized molecular scaffolds, e.g., as described infra. As described in more detail below, solid-phase synthesis of benzoxazoles provides access to highly substituted and functionalized molecular scaffolds, e.g., benzoxazoles, benzothiazoles, etc. in high yield and purity.

DEFINITIONS

The term "benzoxazole," as used herein, refers to 5 membered heteroaromatic compounds which contain a nitrogen atom at a first position of a heteroaromatic ring and an oxygen atom at the third position of the heteroaromatic ring, relative to the nitrogen atom.

The term "benzothiazole," as used herein, refers to 5 membered heteroaromatic compounds which contain a nitrogen atom at a first position of a heteroaromatic ring and a sulfur atom at the third position of the heteroaromtic ring, relative to the nitrogen atom.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein, refers to aryl groups, including 5- and 6-membered single-ring aromatic groups that may include from zero to four heteroatoms, for example, benzene, pyrrole, furan, thiophene, imidazole, benzoxazole, benzothiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" refers to unsaturated aliphatic groups analogous in length and possible substitution to the alkyl groups described above, but that contain at least one double bond.

The terms "alkoxyalkyl", and "thioalkoxyalkyl", refer to alkyl groups, as described above, which further include oxygen or sulfur atoms replacing one or more carbons of the hydrocarbon backbone, e.g., catenary oxygen or sulfur atoms.

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls having one to three carbon atoms.

Suitable organic moieties, such as an aliphatic or aromatic group, which is attached at two positions to two separate organic moieties as defined in $R_1$ include

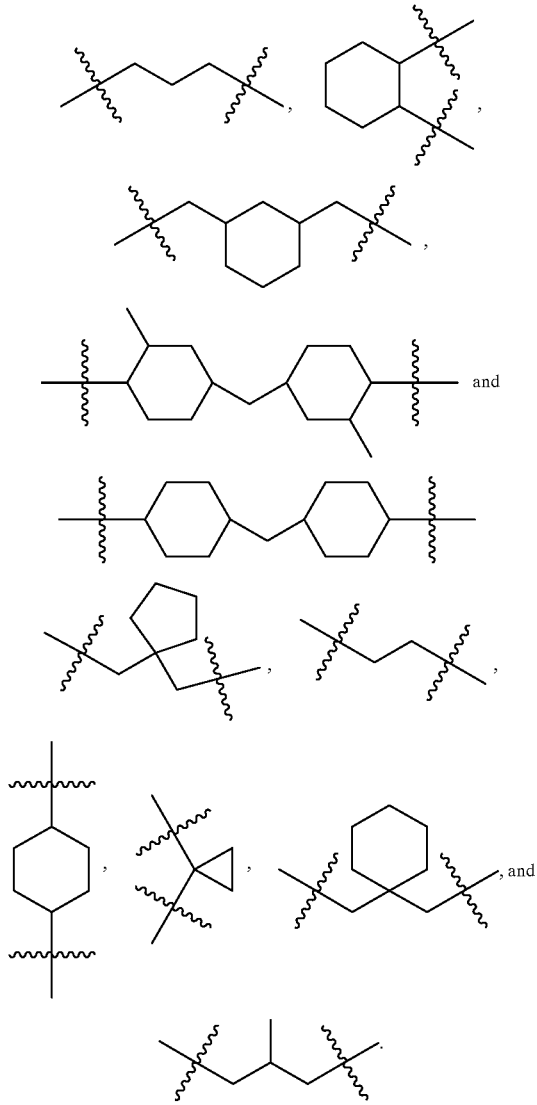

Suitable examples of aryl groups include

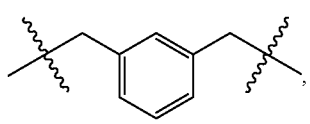

-continued

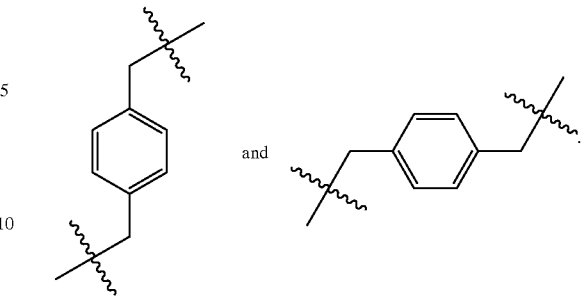

An example of an alkylene group is

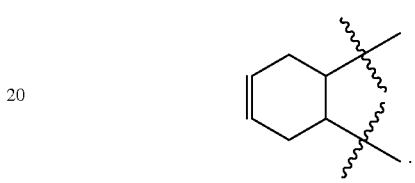

Examples of alkoxyalkyl and thioalkoxyalkyl groups include

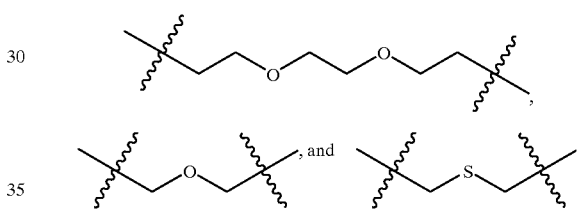

The terms "heterocyclyl" or "heterocyclic group" refer to the group of 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. A heteroalkyl moiety is an alkyl substituted with a heteroaromatic group.

The terms "polycyclyl" or "polycyclic group" refer to the group of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "linker group," as used herein, refers to a linking or spacing moiety which can be used to covalently or non-covalently link a compound to a solid support. The linker group can include the reaction product of an activated resin and a molecule, a linker, which has reacted with the activated resin and still retains functionality which can be further reacted. The linker group can further include the reaction product between an activated solid phase bound linker and a reactive molecule, such as a dicarboxylic acid anhydride or an amino acid in the presence of a coupling reagent. This reaction product, the linker group can include functionality which can then be further reacted with additional species. This process of reacting a solid phase bound linker and a reactive molecule can be repeated, thereby forming a linker group which contains several linkers and reactive molecules. Linker groups suitable for use in the invention are known in the art for use in solid-phase synthesis.

The term "linker," as used herein, refers to a molecule which reacts with a solid support treated with an activation agent, an activated resin or solid support, and still retains functionality within the molecule which can further react with another reactive molecule. It will be appreciated by the skilled artisan that a variety of linkers can be used to covalently (or, in certain embodiments, non-covalently) tether the compounds of the invention to a solid support. Linkers can be selected according to criteria such as length, chemical stability (or lability, where it is desired to cleave the compound from the resin), and the like.

The term "activated resin" or "activated solid support," as used herein, refers to a polymeric resin which has been functionalized with a reagent, an activating agent, to be reactive to linker molecules. For example, treatment of a solid support containing hydroxyl functionality with carbonyldiimidazole (CDI) forms an activated solid support functionalized with an imidazoyl carbamate. The surface of the solid support is thereby rendered reactive to certain types of nucleophilic molecules, such as diamines, which are linkers. FIG. 1 depicts the various groups associated with an activated resin.

The term "solid support" is known in the art and, as used herein, refers to a solid or insoluble material suitable for solid phase synthesis of the compounds of the invention. The solid support can be a particle such as a bead, or a surface, such as a chip or wafer. In general, a solid support will be an inorganic or polymeric organic matrix, such as are known in the art. A variety of solid supports are known in the art (for examples, see, e.g., M. Bodansky "Principles of Peptide Synthesis", 2nd edition, Springer-Verlag, Berlin (1993); Hauske, J. R.; Dorff, P. *Tetrahedron Lett.* 1995, 36, 1589; and references cited therein). Many such art-recognized solid supports are useful in the methods of the invention. For example, solid supports suitable for use in the present invention include suitably modified forms of: silica (e.g., particles such as silica gel), silicon (e.g., wafers or chips), glass (e.g., a glass plate or controlled pore glass beads), polystyrene, polystyrene/divinylbenzene copolymer, polyacrylamide, Tenta-Gel, Wang resin, Rapp resin, Merrifield resin, Rink resin, and the like.

Figure 2:
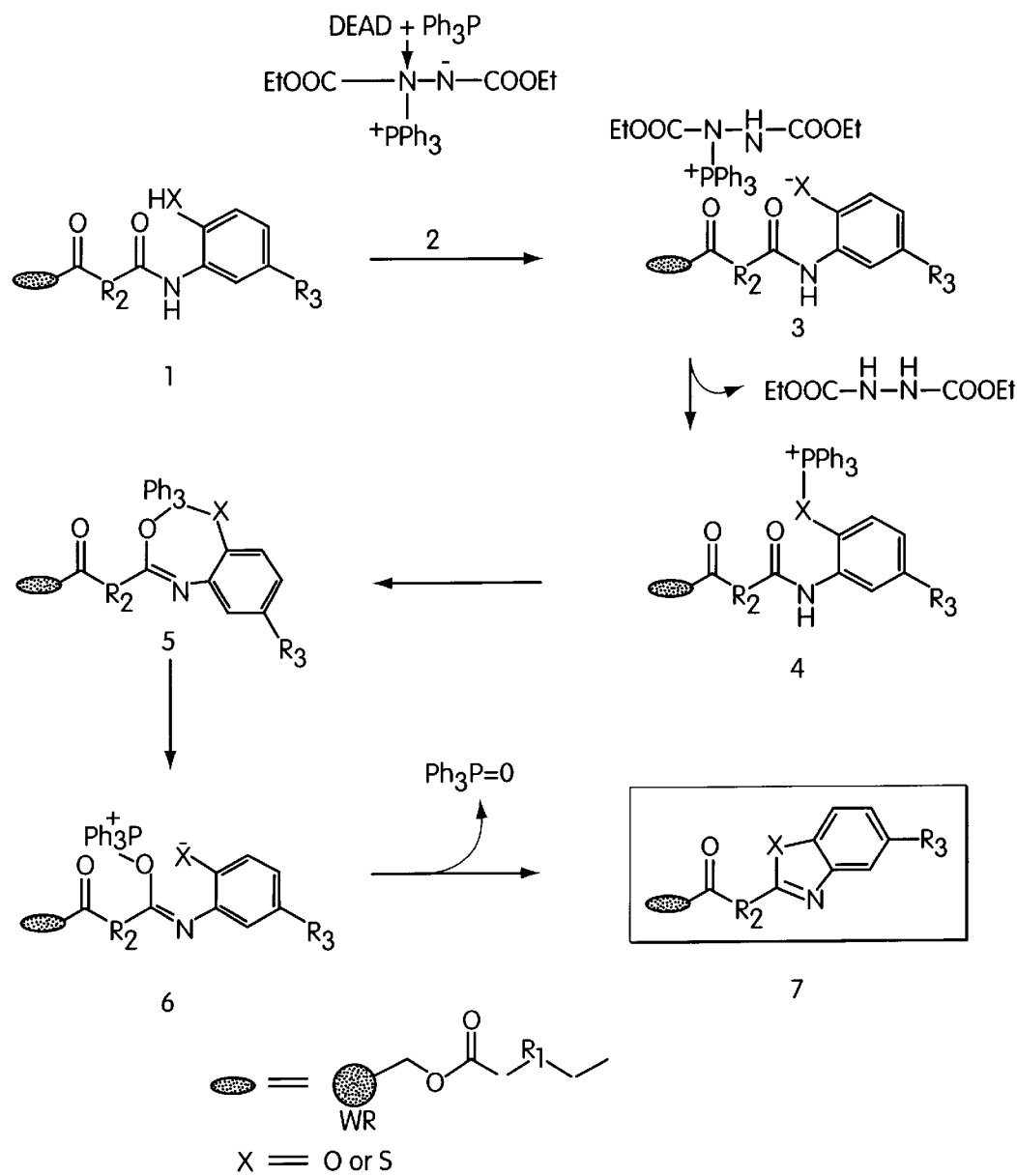
FIG. 2 is a mechanistic outline for cylization-dehydration.

The term "cyclization-dehydration reagent", as used herein, refers to a compound or compounds capable of causing a phenolic or thiophenolic group to condense with an amide carbonyl carbon with subsequent dehydration. For example, FIG. 2, provides a plausible pathway for cyclization-dehydration of a phenol or a thiophenol with an amide carbonyl by treatment with diethylazodicarboxylate and triphenyl phosphine. These reagents are suitable in solution phase synthesis and are especially useful for solid phase synthesis of benzoxazoles and benzothiazoles. Cyclization-dehydration agents for use in solution phase synthesis include polyphosphoric acid (PPA) (Suto, M. J.; Turner, W. R. *Tetrahedron Lett.* 1995, 36, 7213; and Haugwitz, R. D.; Angel, R. G.; Jacobs, G. A.; Maurer, B. V.; Narayanan, V. L.; Cruthers, L. R.; Szanto, J. *J. Med. Chem.* 1982, 25, 969) propionic acid (Nestor, J. J.; Norner, B. L.; H, T. L.; Jones, G. H.; McRae, G. I.; Vickery, B. H. J. Med Chem. 1984, 27, 320; thionyl chloride ($SOCl_2$) (Stack, J. G.; Curran, D. P.; Geib, S. V.; Rebek, J.; Ballester, P. J. Am. Chem. Soc. 1992, 114, 7007); pyridine, p-toluenesulfonate, xylene at reflux (Godstein, S. W.; Dambek, P. J. J. Heterocyclic Chem. 1990, 27, 335; and $POCl_3$ (Orjales, A.; Bordell, M.; Rubio, V. J. Heterocyclic Chem. 1995, 32, 707).

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

The term "subject," as used herein, refers to an animal, more preferably a warm-blooded animal, most preferably a mammal, including cattle, sheep, pigs, horses, dogs, cats, rats, mice, and humans.

The term "treating a bacterial infection," as used herein, refers to preventing an infection, preventing spread of an infection, or decreasing the extent or severity of a bacterial infection. In a preferred embodiment, the bacterial infection is cured, i.e., substantially eliminated.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

I. Compounds

In one aspect, the invention provides compounds represented by the formula (Formula V):

(V)

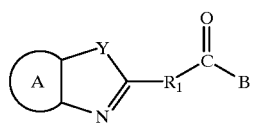

and salts thereof, wherein A is a substituted or unsubstituted aryl and Y is O or S. $R_1$ is a substituted or unsubstituted moiety that is bonded at least to a benzoxazole or benzothiazole group and the group (C↑O)B. More specifically, $R_1$ is a linear or branched alkyl group, an alkenyl group, an alkoxyalkyl group, a thioalkoxyalkyl group, or an aryl group. Suitable examples of $R_1$ include

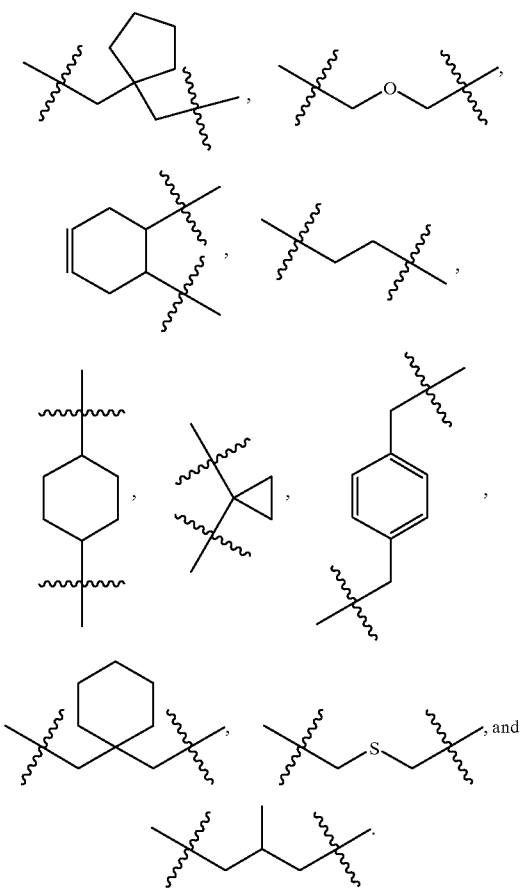

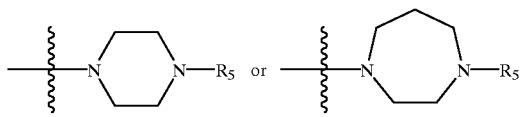

B is —N($R_2$)$R_3$N($R_4$)($R_5$), wherein $R_2$ is a hydrogen atom and $R_3$ is a linear or branched, substituted or unsubstituted alkyl diradical. $R_4$ and $R_5$ are each independently a hydrogen atom, a linker group attached to a solid support, or $R_2$ and $R_4$ taken together represent a substituted or unsubstituted cycloalkyl group. In a preferred embodiment, B is

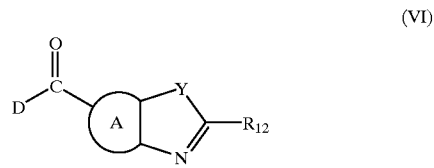

In one embodiment, $R_3$ is an alkyl group. In another embodiment, A is a substituted aryl group and can be substituted with one or more substituents, wherein each substituent is either $CH_3$—, $(CH_3)_3C$—, $C_6H_5$—, $CH_3CH_2SO_2$—, Cl—, or $NO_2$—.

In a preferred embodiment, a substituted aryl group includes a substituent located para to Y in Formula V.

In another aspect, the invention provides compounds represented by the formula (Formula VI):

(VI)

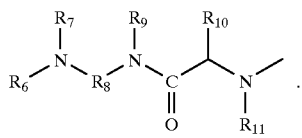

and salts thereof, A is an aryl group and Y is O or S. D is

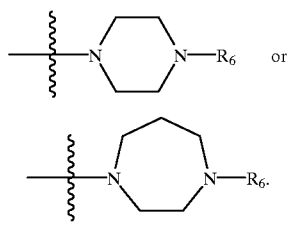

In one embodiment, D is

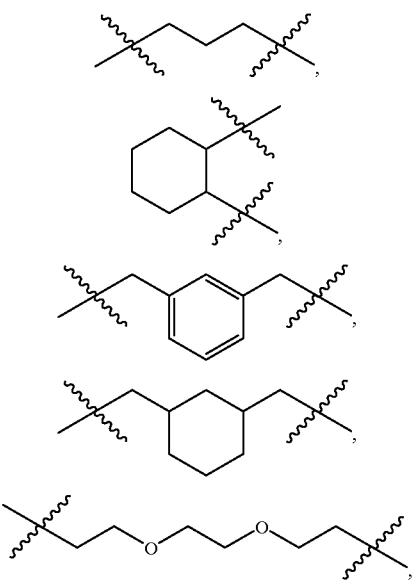

$R_6$ and $R_7$ are each independently a hydrogen atom or a linker group to a solid support. $R_8$ is a substituted or unsubstituted moiety that is bonded at least to $NR^6R^7$ and $NR^9$. More specifically, $R_8$ is a linear or branched alkyl group, an aryl group, or an alkoxyalkyl group. Suitable examples of $R_8$ include -continued

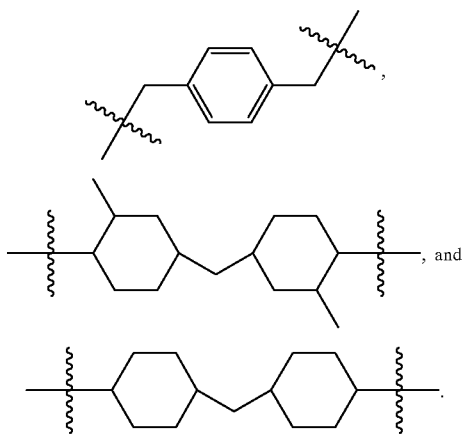

$R_9$ is a hydrogen atom or $R_7$ and $R_9$ when taken together represent a cycloalkyl group. Rlo is a linear or branched, substituted or unsubstituted alkyl group or substituted or unsubstituted aryl group. Suitable examples include methyl, iso-propyl, butyl, toluyl, methyl-2-thioethyl, methylol, acetate, 3-aminopropyl, 4-aminobutyl, 2- methylpropyl, and prolinyl groups.

$R_{11}$ is a hydrogen atom. $R_{12}$ is a linear or branched, substituted or unsubstituted alkyl group, a linear or branched, substituted or unsubstituted alkenyl group,or a substituted or unsubstituted aryl group. Suitable examples include p-methoxy-toluyl, toluyl, 2-ethylbenzyl, 3-methylpyridyl, 2-cyclopentylethyl, 4-methylcyclohexyl, cyclohexyl, 1-methyladamantyl, 2, 2-diphenylethyl, p-phenyl-toluyl, 2-methylthiophenyl, alpha-methylnaphthalenyl, 3,4,5-trimethoxytoluyl, 2-methyl-3-methyl-indolyl, 2-fluorotoluyl, 4-methylpyridinyl, anisolyl, cyclopropyl, 2-methylcyclopropyl, 4-methoxycyclohexyl, tetrahydrofuryl, ethylbenzene, 3-bromopropyl, 1-butenyl, methyl, iso-propyl, butyl, toluyl, methyl-2-thioethyl, methylol, acetate, 3-aminopropyl, 4-aminobutyl, 2-methylpropyl, propyl, 3-methoxytoluyl, ortho-xylyl, para-xylyl, ortho-nitrotoluyl, para-nitrotoluyl, phenylcyclopropyl, tert-butyl, para- trifluoromethanetoluyl, ethylcyclohexyl, 6-methoxymethanenaphthalenyl, 3-methoxycyclohexyl, 2-methylcyclohexyl, ortho-trifluoromethanetoluyl, and 3-methylcyclohexyl groups.

It will be appreciated by the skilled artisan that for the compounds of Formula V and Formula VI, when $R_5$ and $R_6$, respectively, are bonds between terminal nitrogen atoms and solid supports, the bond between $R_5$ and $R_6$ and the solid support can be disrupted under appropriate conditions, e.g., by treatment with trifluoroacetic acid, as is known in the art. In one embodiment, $R_5$ and $R_6$ is a bond between the terminal nitrogen atom and that portion of an activating agent which remains attached to a solid support after coupling.

In preferred embodiments, the compound of Formula V or VI is substantially pure, i.e., the compound is at least 80%, 90% or 95% pure. Compounds which are not substantially pure can be purified by conventional methods, including the methods described infra.

The compounds of the invention can have a variety of closely spaced functionalities and may serve as interesting molecular scaffolds. For example, certain compounds of the invention have anti-bacterial activity, can act as $5-HT_2$ inhibitors, as elastase inhibitors, and as antifungal agents. For example, certain compounds of the invention have activity against gram-positive bacteria. In particular, certain compounds of Formula I, III, V, and VI are useful as anti-bacterial agents, and certain compounds of Formula V are useful as anti-fungal agents and as $5-HT_2$ inhibitors, and as antibacterial agents.

Examples of antibacterial and anti-fungal agents prepared by the methods of the present invention include:

IX
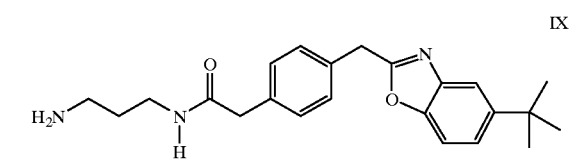

XX
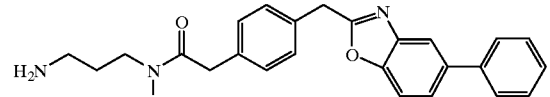

XI
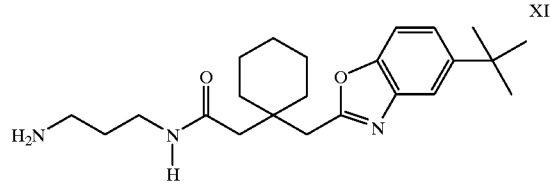

XIII
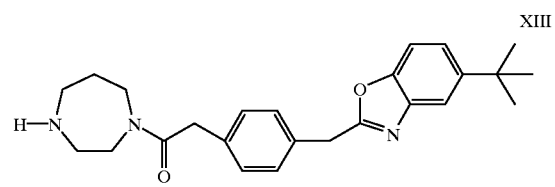

XIV
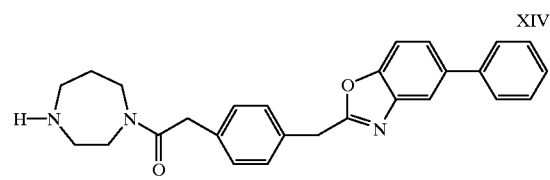

XV
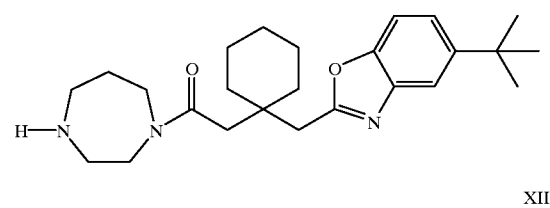

XII
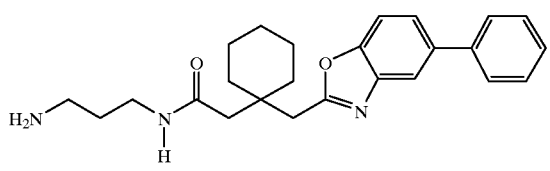

XVII
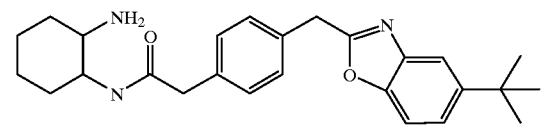

XVIII
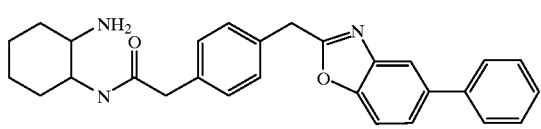
XXV
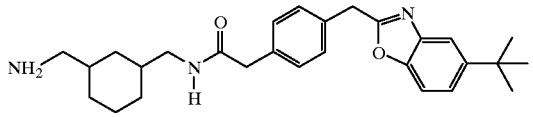
XXIV
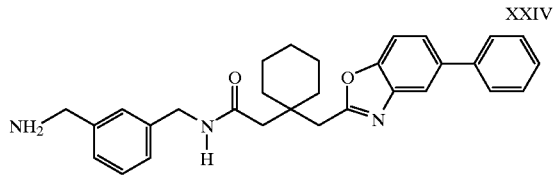
XIX
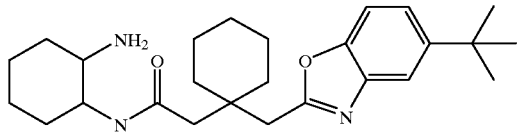
XVI
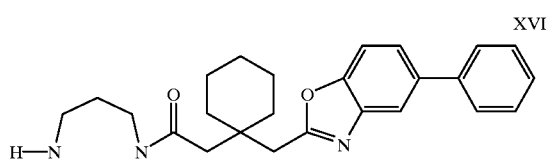
XXVI
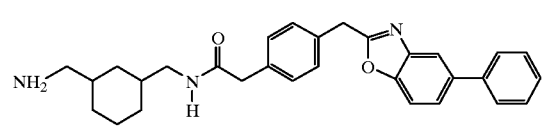
XX
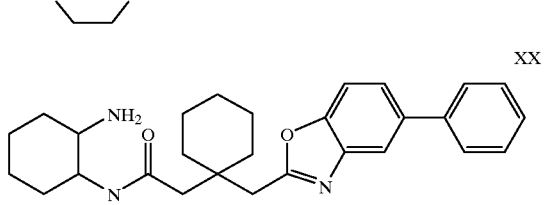
XXVII
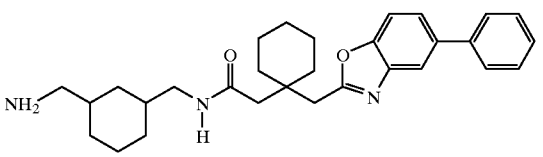
An example of a 5-HT$_2$A inhibitor prepared by the method of the present invention is:
XXII
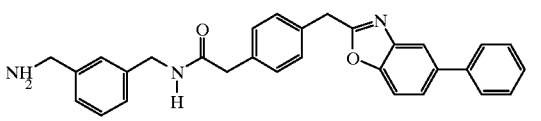
XXIX
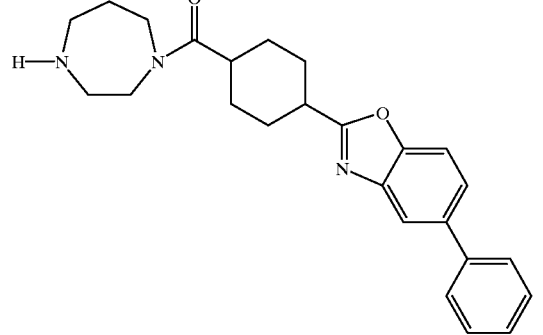
XXIII
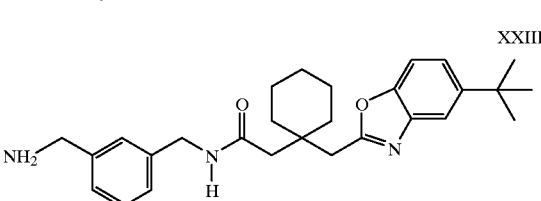
XXIV
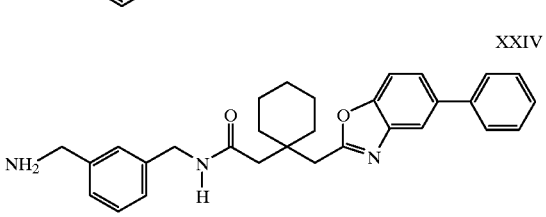
Suitable examples of human neutrophil elastase inhibitors include:
XXX
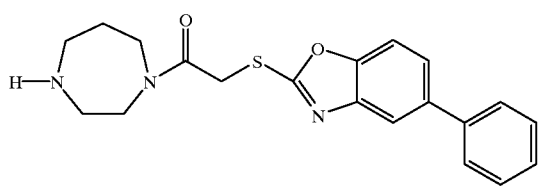
XXXI
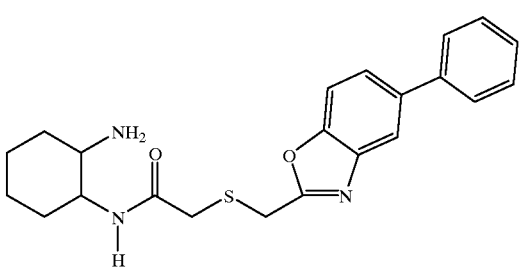

-continued

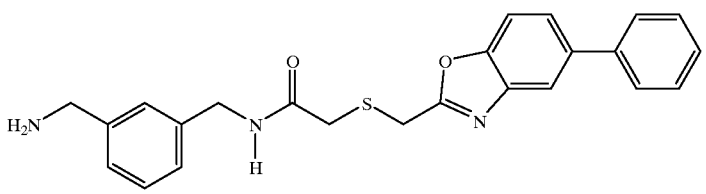

XXXII

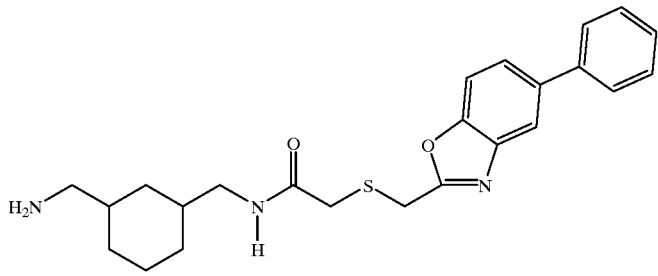

XXXIII

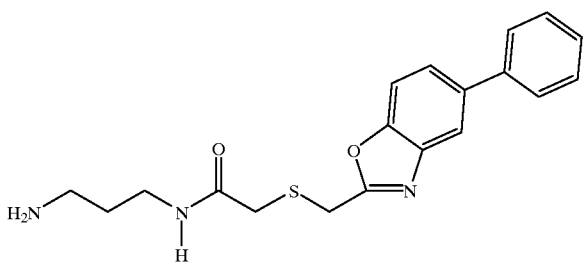

XXXIV

II. Methods

In another aspect, the invention provides methods for preparing the compounds of the invention, and methods for inhibiting microbial growth.

In one embodiment, the invention provides a method for preparing a compound represented by the formula (Formula I)

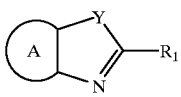

(I)

A is a substituted or unsubstituted aryl or heteroaryl group and Y is O or S. $R_1$ is a linear or branched, substituted or unsubstituted alkyl group, a substituted or unsubstituted aryl group, or a linker group attached to a solid support, or a salt thereof. The method includes reacting a compound having the formula (Formula II):

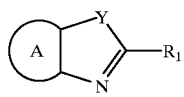

(II)

wherein Y is O or S, with a cyclization-dehydration reagent under suitable conditions such that a compound of Formula I is formed.

Figure 3:
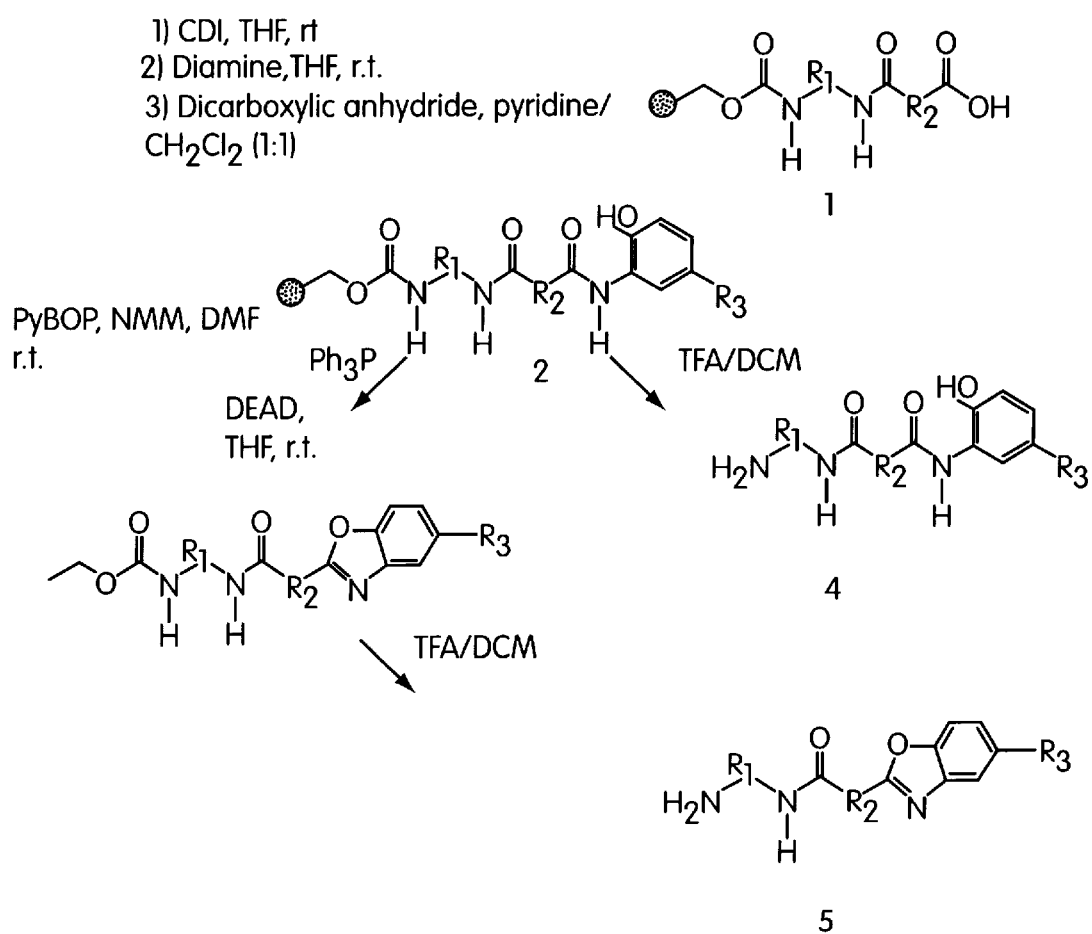
FIG. 3 is a representative synthesis of the compounds of the invention.

In an illustrative scheme, (see FIG. 3), a hydroxyl bearing resin (e.g. Wang Resin) is reacted with an activating agent, such as (CDI), to form an activated solid support (e.g. Hauske support). Reaction of the activated solid support with a linker, such as diamine (e.g., propane-1,3-diamine) followed by treatment with a dicarboxylic anhydride, a reactive molecule, provides functionalized amide 1, the linker group. The reaction progress can be monitored by the Kaiser test, Kaiser, E.; Colescott, R. L.; Bossinger, C. D.; Cook, P.I.; *Analyt. Biochem.* 1970, 84, 595, in which the support substrate should be colorless for complete reaction.

Amide 1 is then reacted with a 2-aminophenol under coupling conditions to provide resin 2. Intramolecular cyclization-dehydration of the amide phenol attached to solid support (resin 2) where excess triphenyl phosphine (TPP) and diethylazodicarboxylate (DEAD) are employed, provides resin 3. Treatment of resin 2 under hydrolytic conditions affords compound 4. Representative examples include 4a–4b listed below.

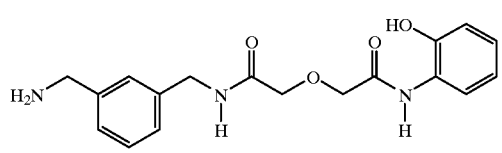

4a

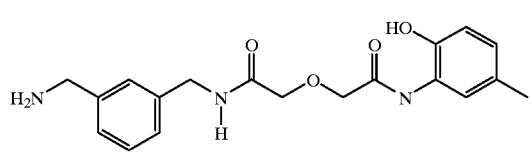

4b

-continued

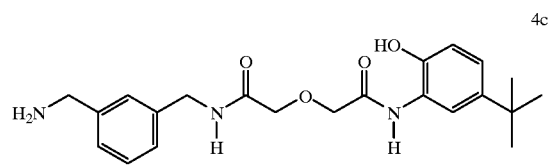
4c

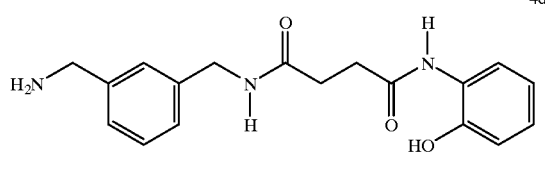
4d

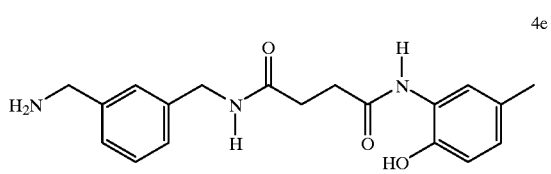
4e

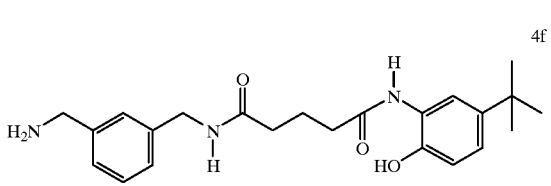
4f

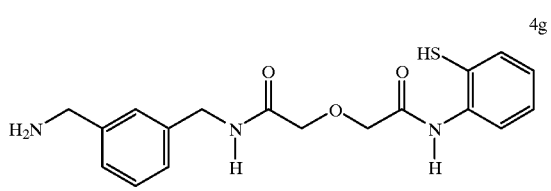
4g

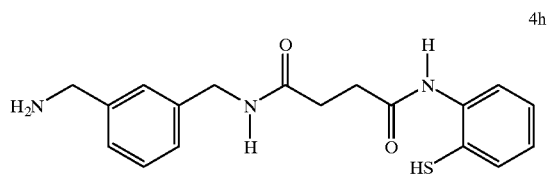
4h

Alternatively, cleavage of the heterocycle (e.g., benzoxazole) from resin 3 provides compounds 5, as shown in representative formulae 5a–5h.

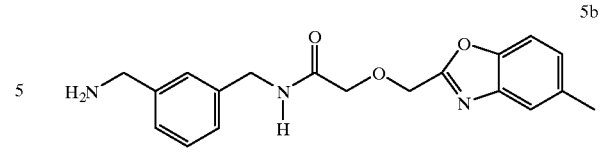
5a

N-(3-aminoethylbenzyl)--(2-benzoxazolylmethoxy) acetic amide

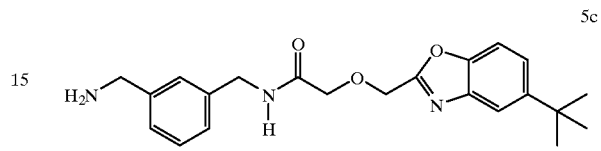
5b

N-(3-aminomethylbenzyl)--[2-(5-methyl-benzoxazolylmethoxy)] acetic amide

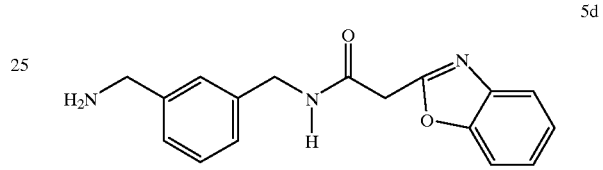
5c

N-(3-aminomethylbenzyl)--[2-(5-t-butyl-benzoxazolyl-methoxy)] acetic amide

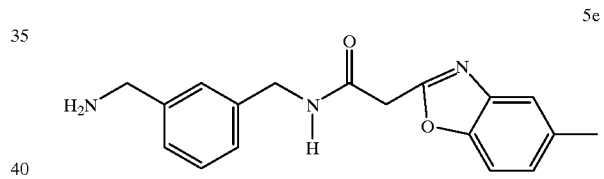
5d

N-(3-aminomethylbenzyl)-3-(2-benzoxazolyl) propionic acid

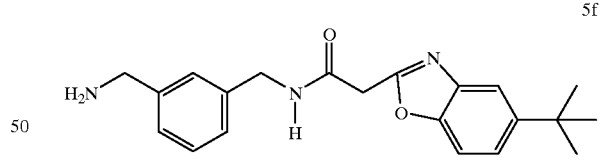
5e

N-(3-aminomethylbenzyl)-3-[2-(5-methylbenzoxazolyl)] propionic amide

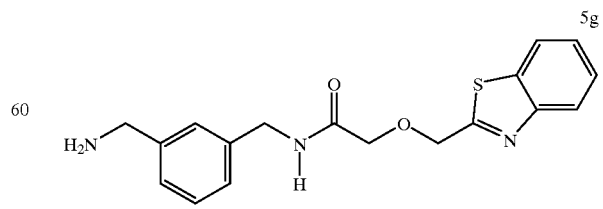
5f

N-(3-aminomethylbenzyl)-3-[2-(5-tert-butylbenzoxazolyl)] propionic amide

5g

N-(3-aminomethylbenzyl)--(2-benzothiazolylmethoxy) acetic amide

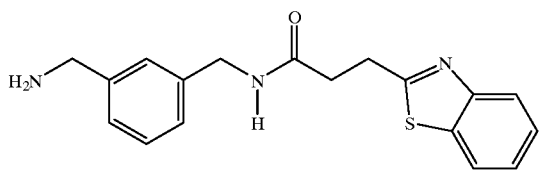

N-(3-aminomethylbenzyl)-3-(2-benzothiazolyl) propionic amide

In another embodiment, the invention provides the method of preparing a compound represented by the formula (Formula III):

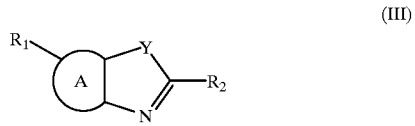

(III)

A is a substituted or unsubstituted aryl or heteroaryl group and Y is O or S. $R_1$ is a linear or branched, substituted or unsubstituted alkyl group, a substituted or unsubstituted aryl group, or a linker group attached to a solid support. $R_2$ is a linear or branched, substituted or unsubstituted alkyl group, a substituted or unsubstituted aryl group, or a salt thereof. The method includes reacting a compound having the formula (Formula IV)

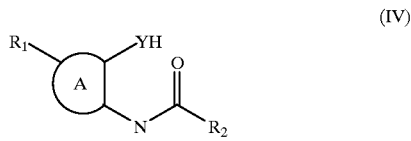

(IV)

wherein Y is O or S, with a cyclization-dehydration reagent under suitable conditions such that a compound of Formula III is formed.

Figure 4:
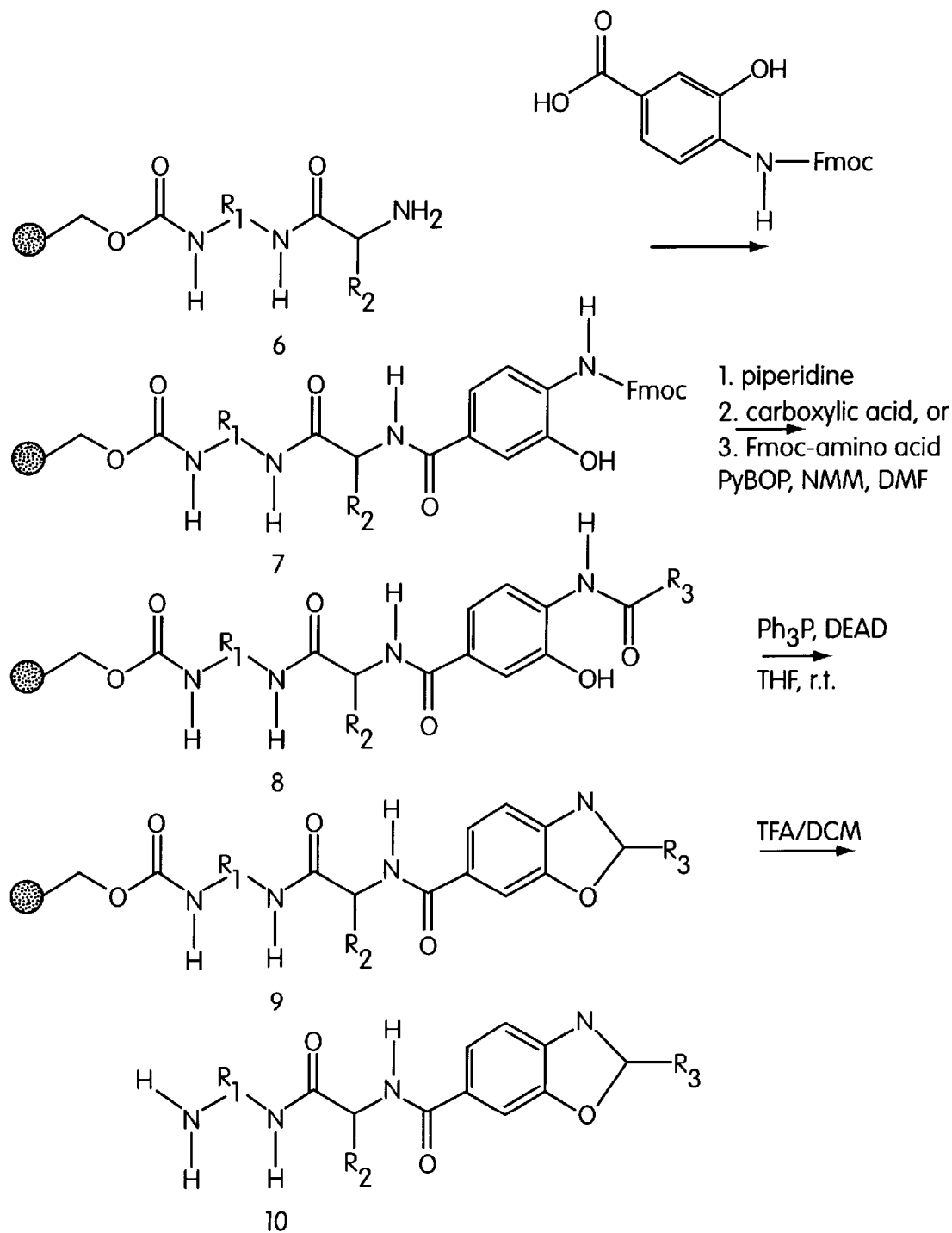
FIG. 4 is another representative synthesis of the compounds of the invention.

In an illustrative scheme, (see FIG. 4), a hydroxyl bearing resin (e.g. Wang Resin) is reacted with an activating agent, (CDI), to form an activated support (e.g., Hauske support). Reaction of the activated support with a diamine, a linker, (e.g., propane-1,3-diamine) followed by treatment with a amino acid provides functionalized amide 6 as an linker group. Amide 6 is then reacted with a 3-hydroxy-4-protected amino benzoic acid, such as 4-(N-Fmoc)-amino-3- hydroxy benzoic acid, under coupling conditions to provide resin 7. Removal of the amine protecting group to afford intermediate 8 followed by intramolecular cyclization-dehydration of the amide phenol attached to solid support with excess TPP and DEAD, provides resin 9. Cleavage of the heterocycle (e.g., benzoxazole) from resin 9 provides compound 10.

In certain embodiments, the method of the invention includes the further step of purifying the compound of Formula I, II, III or IV (e.g., by washing the solid support upon which the compound is immobilized). In certain embodiments, the method includes the further step of cleaving the compound of Formula I or Formula III from the solid support. In certain embodiments, the method includes the step of purifying the compound (or compounds) produced in the cyclization-dehydration reaction. In certain embodiments, the compound or compounds of Formula I and/or Formula III can be further reacted, e.g., to produce derivatives and analogs of compounds of Formula I and/or Formula III.

The methods of the invention provide several advantages over reactions previously reported for the synthesis of benzoxazoles. Known preparations of benzoxazoles from 2-heteroatom carbamate phenols include methods which are performed under harsh conditions, such as for example, polyphosphoric acid (PPA) at 1800 C, propionic acid at 140°; phosphoryl chloride ($POCl_3$) at ref lux and thionyl chloride ($SOCl_2$) in the presence of pyridine in xylene at reflux. Under such harsh conditions, the polymer support does not survive or the heteroatom phenol is cleaved from the support.

The reaction conditions of the invention are mild. Generally the 2-aminophenol or 2-aminothiophenol is treated with an excess (e.g., 5 equivalents) of TPP and DEAD at room temperature. Furthermore, the cyclization- dehydration reactions of the invention proceed without unwanted side reactions and in good yield. The products can be easily and quickly isolated and purified, often by simply filtering the solid support, washing to remove unwanted impurities, and cleaving the product from the solid support.

III. Linker Groups

Linker groups useful for immobilizing compounds on a solid support are well known in the art and include, e.g., diamino linkers, phenylene moieties, and the like. A particularly preferred linker group is the linker group described in Hauske, J. R.; Dorff, P. *Tetrahedron Lett.* 1995, 36, 1589. This linker group, the reaction product between an CDI activated solid support and a diamine, is easily synthesized, stable under a variety of reaction conditions, and readily cleaved to release the product from the solid support.

A particularly preferred linker group of the present invention is the reaction product between a diamine treated activated solid support and a dicarboxylic acid anhydride or an amino acid with a coupling reagent. This linker group therefore contains functionality which can be synthetically modified. After synthetic modifications have been completed, the linker group, or a portion of the linker group can be cleaved to release the product from the solid support.

It will be understood that the linker can be selected to have a length which permits facile reaction with a substrate compound immobilized on a solid support. For example, the linker should be long enough to avoid steric encumbrance of the immobilized compound by the solid support. The linker can be selected to be cleavable under a variety of conditions (e.g., hydrolytic, nucleophilic, electrolytic, oxidative, photolytic, and the like), if desired, as is known in the art. The skilled artisan will appreciate that the choice of linker, in combination with the choice of solid support, can influence factors such as reaction time, completeness of reaction, releasability of the reaction products, and the like. Thus, the linker and solid support will in general be selected to permit ready immobilization, reaction, isolation, and purification of the compounds of the invention.

Suitable linkers include:

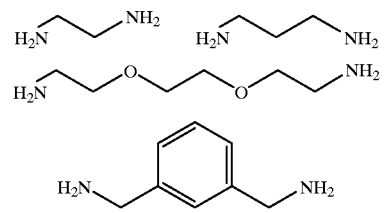

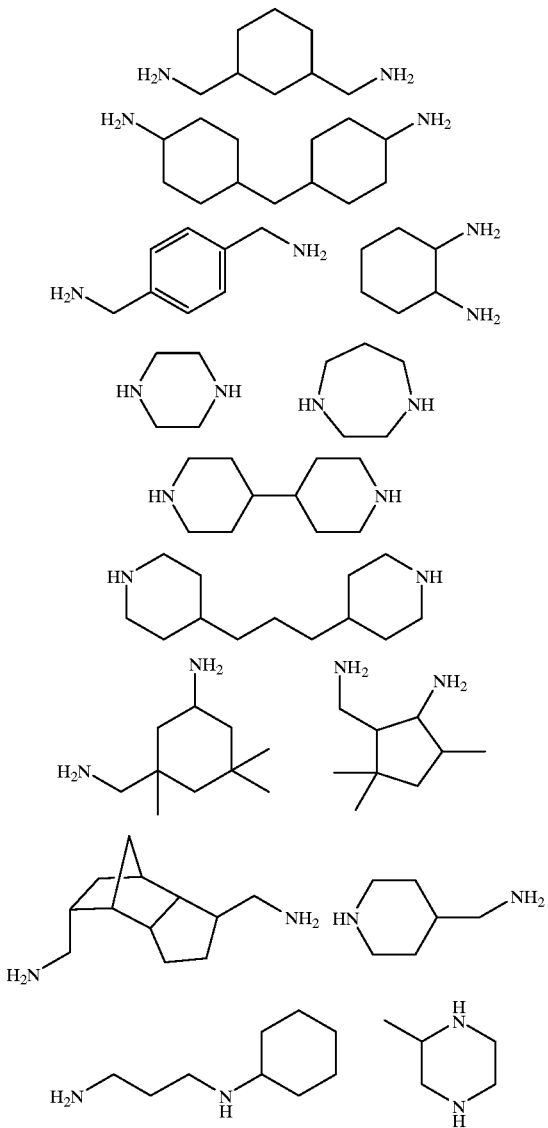

Reaction conditions

The reactions of the present invention may be performed under a wide range of conditions, though it will be understood that the solvents and temperature ranges recited herein are not limiting and only correspond to a preferred mode of the process of the invention.

In general, it is desirable that reactions are run using mild conditions that will not adversely affect the starting materials, the intermediates, the resin, the linker, the activated resin, the linker group or the products. For example, the reaction temperature influences the speed of the reaction, as well as the stability of the reactants and the activated resin. The reactions will usually be run at temperatures in the range of −78° C. to 100° C., more preferably in the range −20° C. to 50° C. and still more preferably in the range −20° C. to 25° C.

In general, the reactions according to the invention will be performed in a liquid medium, e.g., in a suspension of an activated solid support in a liquid medium. The reactions may be run in an inert solvent, preferably one in which the reaction ingredients, optionally including the polymeric support, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. The reactions can be conducted under anhydrous conditions, and in certain embodiments it is preferable to perform the reactions under an inert atmosphere of a gas such as nitrogen or argon.

The progress of the reaction can be monitored by techniques known to one of ordinary skill in the art. For example, aliquots of the reaction mixture can be taken at intervals and the aliquots tested, e.g., by cleavage of compounds from the solid activated support followed by spectroscopic analysis of the crude reaction mixture. Alternatively, the reaction can be monitored by chromatographic techniques such as thin-layer chromatography (TLC) or HPLC. Additionally, the disappearance of a reactant or reactants can also be monitored by techniques known to a person skilled in the art.

In certain embodiments, the methods for preparing compounds include the further step of purifying the compounds. Purity of the reaction products can be determined according to known techniques. If the products are impure, they can be determined according to known techniques. If the products are impure, they can be purified according to a variety of methods known in the art. For example, compounds immobilized on a solid support can be separated from some impurities by simple filtration and washing of the solid support to remove soluble impurities. Compounds which are not immobilized on solid supports can be purified by methods including crystallization (where the compound is crystalline), trituration, distillation, and chromatographic techniques such as TLC and HPLC (analytical or preparative scale), flash chromatography, and the like. The selection of methods for purifying compounds will be routine for the ordinarily skilled artisan.

In preferred embodiments, the purity of a compound produced according to the methods of the invention is at least about 50%, more preferably at least about 70%, still more preferably at least about 90%, and most preferably at least about 95%.

In another aspect, the invention provides methods for treating bacterial infections, methods for inhibiting elastase activity, methods of inhibiting 5-$HT_2$ activity, and methods of treating anti-fungal agents. Conditions that can be treated through inhibition of elastase activity include bronchitis and cystic fibrosis. Conditions that can be treated by 5-$HT_2$ inhibition include anxiety and other psychotic conditions. Bacterial infections which can be treated according to the methods of the invention include (but are not limited to) infections due to gram-positive bacteria such as *E. Coli* and *Staphylococcus aureus*.

In general, the method comprises administering to a subject in need thereof an effective amount of a compound of the invention, such that the desired effect is obtained. The compound of the invention can be, e.g., a compound of Formula I, Formula III, Formula VII, or Formula VIII and can optionally be administered in a pharmaceutically acceptable vehicle. It will be understood that more than one compound of the invention can be employed to treat a bacterial infection; such multi-drug therapy can be useful to provide a broader spectrum of action against bacterial or to prevent the development of drug-resistant bacterial strains.

As is described in more detail below, a compound of the invention can be administered to a subject topically, e.g., to treat a localized bacterial infection, or systemically, e.g., to treat a systemic bacterial injection. A compound of the invention is preferably administered such that the bacterial infection is cured.

IV. Libraries

In another aspect, the invention provides libraries of compounds of Formula V and VI and methods of preparing such libraries.

The synthesis of combinatorial libraries is well known in the art and has been reviewed (see, e.g., E. M. Gordon et al., *J. Med. Chem.* 37:1385–1401 (1994)). Thus, the subject invention contemplates methods for synthesis of combinatorial libraries of compounds of Formula V or VI. Such libraries can be synthesized according to a variety of methods. For example, a "split-pool" strategy can be implemented in the following way: beads of a functionalized (activated) polymeric solid support are placed in a plurality of reaction vessels. To each aliquot of beads is added a solution of a different diamine, and the reactions proceed to yield a plurality of immobilized diamines, i.e., the linking group. The aliquots of derivatized beads are then washed, "pooled" (i.e., recombined), and the pool of beads is again divided, with each aliquot being placed in a separate reaction vessel. To each reaction vessel is added a solution of a different dicarboxylic acid anhydride or an amino acid and a coupling reagent to yield a plurality of reaction vessels each containing a plurality of compounds of Formula II or IV immobilized on a solid support. The derivatized amide is then treated with a cyclization-dehydration reagent to form an benzoxazole of Formula I, III, V or VI. The library of immobilized compounds can then be washed to remove impurities. In certain embodiments, the compound of Formula V or VI can further be treated (e.g., by cleavage, if desired, and cyclization) to yield hydrolyzed products of Formulae V or VI.

In another illustrative method of combinatorial synthesis, a "diversomer library" is created by the method of Hobbs, DeWitt et al. (*Proc. Natl. Acad. Sci. U.S.A.* 90:6909 (1993)). Aliquots of activated polymeric support beads are placed in an array of reaction vessels, and one of a plurality of diamines is introduced into each vessel. After reaction, the beads are washed to yield an array of immobilized amine intermediates. Each vessel in the array is then reacted with one of a plurality of dicarboxylic acid anhydrides or amino acids with a coupling reagent. After cyclization-dehydration, purification and workup yields a soluble library of substituted compounds of Formula I, III, V or VI.

Other synthesis methods, including the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med. Chem., op. cit.*). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are known in the art (see, e.g., E. M. Gordon et al., *J. Med. Chem.* 37:1385–1401 (1994)).

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 30 compounds, more preferably at least 100 compounds, and still more preferably at least 500 compounds. In preferred embodiments, the libraries of compounds of the invention contain fewer than 109 compounds, more preferably fewer than 108 compounds, and still more preferably fewer than 107 compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably at least about 90%, and most preferably at least about 95%.

The libraries of the invention can be prepared according to the methods of the invention, wherein at least one of the diamine and the dicarboxylic acid anhydride or amino acid and coupling reagent is provided as a variegated population. The term "variegated population", as used herein, refers to a population including at least two different chemical entities, e.g., of different chemical structure. For example, a "variegated population" of diamines would comprise at least two diamines. Similarly, a variegated population of dicarboxylic acid anhydrides or amino acids comprises at least two different dicarboxylic acid anhydrides or amino acids. Use of a variegated population of linkers can produce a variety of compounds upon cleavage of the linkers.

Libraries of the invention are useful, e.g., for drug discovery. For example, a library of the invention can be screened (e.g., according to the methods described herein) to determine whether the library includes compounds having a pre-selected activity. Thus, for example, a library can be screened to determine whether compounds of the library have anti-bacterial activity or any other activity which can be detected in vitro or in vivo, e.g., anti-inflammatory activity, enzyme inhibitory activity, and the like.

V. Pharmaceutical compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: oral administration, for example, drenches (aqueous or non-aqueous solutions or suspensions), tablets, boluses, powders, granules, pastes for application to the tongue;

parenteral administration, for example, by subcutaneous, intramuscular or intravenous injection as, for example, a sterile solution or suspension; topical application, for example, as a cream, ointment or spray applied to the skin; or intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect by treating (i.e., preventing or ameliorating) a bacterial infection in a subject, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (see, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra.)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the peptidomimetic in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The invention is further illustrated by the following examples which in no way should be construed as being further limiting. The contents of all references, pending patent applications and published patent applications, cited throughout this application are hereby incorporated by reference. The models used throughout the examples are accepted models. The demonstration of efficacy in these models is predictive of efficacy in humans.

Exemplification

Measurement of Antimicrobial Activity

Modified Kirby-Bauer Susceptibility Testing (see, e.g., Finegold et al. "Diagnostic Microbiology," 6th Ed., C. V.

Mosby Co., St. Louis, (1982), pp. 542–543: Microorganisms are grown on a solid medium in order to ensure a pure homogeneous culture. This requires an 18–24 hour grow out. Once purity is determined, the microorganism is subcultured by picking off one to three colonies from the solid medium using a sterile loop, and placing the colonies onto an appropriate liquid medium (e.g., Brain Heart Infusion for bacteria and Sabouraud's Dextrose for yeast or fungi). The microorganisms are then allowed to grow for 4–6 hours at the appropriate atmospheric and temperature conditions. After the 4–6 hour grow out, the microorganisms are ready for testing.

The microorganisms are grown to a standard density (turbidity) by diluting the microorganisms with additional liquid growth medium until their density is comparable to a 0.5% MacFarland standard. The MacFarland standard is prepared by mixing Barium Chloride with sulfuric acid in the appropriate proportions, as is known in the art (see, e.g. Finegold et al., supra). Once the cultures have been standardized, sterile cotton swabs are used to apply the microorganisms to agar plates for testing. The plates are swabbed in three different directions, rotating the plates 60 each time. After the microorganisms have been applied to the plate, 10–12 paper disks (¼") in diameter are spaced evenly around the plate. Compounds to be tested are then dissolved in DMSO and pipetted (101) onto the papers. The plates are then incubated for 24–48 hours depending on the microorganism. The plates are then removed from incubation and observed for zones of inhibition around each of the paper disks. The zones are measured in millimeters and recorded. In general, a zone of inhibition of less than about 11 mm indicates low anti-microbial activity, while a zone of about 11–15 mm indicates moderate activity, and a zone of about 16 mm or greater indicates good activity.

Measurement of 5-$HT_2$ Antagonist Activity

Inhibition of 5-$HT_2$ can be monitored by the R-SAT (Receptor Selective and Amplification Technology, product number 0052, Receptor Technologies, Inc.) method. NIH 3T3 cells expressing rat 5-$HT_2$ receptor cells allow measurement of ligand affinity, agonism and antagonism, as well as differentiation of full and parital agonists. (Pritchett, D. B. et al. EMBO J. 7:4135, (1988); Messier, T. et al. Pharmacol. and Toxicol. 76:308 (1995); Brann, M. R. et al. J. Biomol. Screening 1:43 (1996)).

Measurement of Human Neutrophil Elastase Activity

A buffer solution containing 0.1 M NaCl, 0.01 M HEPES, 0.01 M TRIS, 0.1% PEG 8000 at a pH of 8.0 was prepared. 0.1 ml of buffer was used per reaction.

A sufficient amount of substrate, MeO-Suc-Ala-Ala-Pro-Val-p-nitroanilide (Sigma), was mixed into 10 mL of buffer solution to yield a final concentration of 0.375 mM. 0.1 mL of this solution was placed into a well in a microtiter dish, the compound tested was added to the well to a final cocentration of 1 M and equilibrated for 20 minutes. 0.2 g Human neutrophil elastase (Calbiochem ) was added to the reaction mixture. The resultant mixture was monitored in a microtiter plate reader for 10 minutes (Kinetic, Vmax in mOD/min at a wavelength of 405 nm). Data were compared against reaction rates with no inhibitor present.

General Experimental

Nuclear magnetic resonance (NMR) spectra were recorded using a 300 MHz Varian Unity Fourier transform NMR spectrometer. Low resolution mass spectra (LRMS) were obtained by direct injection of samples in methanol into a single quadrapole mass spectrometer (Finnigan SSQ 7000) equipped with an atmospheric pressure ionization module (APCI-MS). High resolution mass spectroscopy (HRMS) was performed by M-Scan, West Chester, Pa. Elemental analyses were performed by Atlantic Microlabs, Inc., Norcross, Ga.

High pressure liquid chromatography (HPLC) was performed on a Hewlett-Packard 1090 instrument with a $C_{18}$ column (4.6 mm×25 cm) and a diode array detector (peakwidth: 0.53 min, sampling interval: 0.32 min, spectrum from 200–350 nm). A flow rate of 1 mL/min, oven temperature of 40° C. and an injector volume of 4 µL were used. The eluent was a mixture of water and acetonitrile both containing 0.05% TFA. HPLC samples were prepared in water/acetonitrile (1:1). A small amount of methanol was sometimes added to increase solubility. The following two methods were used:

General Methods. The $^1$H and $^{13}$C NMR spectra were recorded on a 300 MHz Varian Inova NMR Spectrometer. Low-resolution mass spectra were obtained by using the ESI technique on Finnigan SSQ 7000 Mass Spectrometer, whole High-resolution mass spectra were obtained by using the FAB technique on VG Analytical ZAB 2SE high field mass spectrometer. The HPLC analyses were performed on a Hewlett Packard 1090 system with a Zorbax C-18 reverse phase column (gradient from 95% of eluent A (0.05% TFA in water) and 5% of eluent B (0.05% TFA in acetonitrile) to 100% of eluent B, flow rate 1.0 mL/min). All starting reagents were of the best grade available (Aldrich, Fluka, Lancaster) and were used without purification. Wang resin (0.75 mmol/g, 100–200 mesh) was obtained from Advanced ChemTech and dried under high vacuum before use.

Preparation of Resin 1. Wang resin was added dry to a solution of 0.4 N of 1,1'-carbonyldiimidazole in anhydrous THF and shaken at room temperature for 6 hours. The resin was washed thoroughly with THF to removed excess CDI and treated with 0.4 N of diamine in THF at room temperature for 15 hours. To the aminofunctionalized resin was added 0.4 N of dicarboxylic anhydride in pyridine/dichloromethene (v:v=1:1) and shaken at room temperature for 2 hours. The resulting carboxylfunctionalized resin 1 was washed with DMF, DCM, and MeOH, and dried under high vacuum. Kaiser test of the beads was negative for complete reaction.

General Procedure for Preparation of Resin 2 and Precursor 4. To resin 1 (100 mg) was added PyBOP (195 mg, 0.375 mmol) (see e.g., Coste et al., Tet. Lett. (1990) 31:205–208) for an example of this coupling procedure) and substituted or unsubstituted 2-aminophenol (0.375 mmol) in 1 mmL of DMF, followed by N-methylmorpholine (NMM) (41 ml, 0.375 mmol). The mixture was shaken at room temperature for 17 hours. The wresting resin 2 was washed extensively with DMF, DCM, and MeOH, and dried under high vacuum. The product in resin 2 was cleaved with TFA/$CH_2Cl_2$ (1:1) at room temperature for 30 minutes , volatiles were removed under a stream of nitrogen, reconstituted into 50% CH3CN in water, frozen and lyophilized, leaving 4 as white or off white powder. The compound was analyzed by HPLC, MS, and NMR.

General Procedure for Preparation of Benzoxazole Derivative 5. To the mixture of resin 2 (100 mg) and $Ph_3P$ (98 mg, 0.375 mmol) in 1 mL of anhydrous THF was added dropwise DEAD (59 l, 0.375 mmol) at room temperature. The mixture was shaken at room temperature for 17 hours, followed by washing with THF, $CH_2Cl_2$, and MeOH. The resin 3 was dried under vacuum, and treated with a solution of 50% TFA in CH2Cl2 for 30 minutes at room temperature to release the polymer-bond heterocycle 5. Removal of the volatiles under a stream of nitrogen followed by Lyophilizing with 50% $CH_3CN$ in water afforded the pure compound as powder.

Amide Phenol (4a) $^1$H NMR (DMSO-d$_6$) 4.02 (dt, J=4.5 Hz, J'=5.7 Hz, 2H), 4.15 (s, 2H), 4.18 (s, 2H), 4.35 (d, J=6.0 Hz, 2H), 6.78 (dd, J=6.0 Hz, J'=7.4 Hz, 1H), 6.90 (d, J=6.0 Hz, 1H), 6.96 (dd, J=5.6 Hz, J'=7.1 Hz, 1H), 7.27–7.38 (m, 4H), 7.89 (d, J=8.1 Hz, 1H), 8.22 (bs, 3H), 8.68 (t, J=6.0 Hz, 1H), 9.15 (s, 1H). $^{13}$C NMR (DMSO-d$_6$) 41.6, 42.3, 70.3, 70.6, 115.3,119.0, 121.6, 124.8, 125.5, 127.2, 127.3, 127.7, 128.7, 134.1, 139.8, 147.7, 167.4, 168.8. MS (ESI) m/z 344.1 (MH$^+$).

Amide Phenol (4b) $^1$H NMR (DMSO-d6) 2.18 (s, 3H), 4.01 (dt, J=5.1 Hz, J'=6.0 Hz, 2H), 4.14 (s, 2H), 4.17 (s, 2H), 4.35 (d, J=6.0 Hz, 2H), 6.77 (s, 2H), 7.29–7.41 (m, 4H), 7.72 (s, 1H), 8.23 (bs, 3H), 8.69 (t, J=6.3 Hz, 1H), 9.11 (s, 1H). $^{13}$C NMR (DMSO-d$_6$) 20.5, 41.6, 42.3, 70.3, 70.6, 122.0, 125.1, 125.2, 127.2, 127.3, 127.6, 127.7, 128.7, 134.0, 139.9, 145.3, 167.2, 168.8. MS (ESI) m/z 358.1 (MH$^+$).

Amide Phenol (4c) $^1$H NMR (DMSO-d$_6$) 1.22 (s, 9H), 4.03 (dt, J=4.5 Hz, J'=6.0 Hz, 2H), 4.15 (s, 2H), 4.18 (s, 2H), 4.36 (d, J=6.0 Hz, 2H), 6.81 (d, J=8.4 Hz, 1H), 6.98 (dd, J=2.4 Hz, J'=8.4 Hz, 1H), 7.29–7.41 (m, 4H), 7.91 (d, J=2.4 Hz, 1H), 8.22 (bs, 3H), 8.66 (t, d=6.3 Hz, 1H), 9.16 (s, 1H). $^{13}$C NMR(DMSO-d6) 31.4, 33.8, 41.6, 42.3, 70.3, 70.6, 121.5, 124.8, 127.3, 127.7, 128.7, 134.0, 139.9, 141.3, 145.5, 167.4, 168.8. MS (ESI) m/z 400.2 (MH$^+$).

Amide Phenol (4d) $^1$H NMR (DMSO-d$_6$) 2.52 (t, J=7.1 Hz, 2Hi), 2.66 (t, J=7.2 Hz, 2H), 4.00 (dt, J=5.4 Hz, J'=6.0 Hz, 2H), 4.28 (d, J=5.4 Hz, 2H), 6.75 (dd, J=8.1 Hz, J'=8.7 Hz, 1 H), 6.85 (d, J=8.1 Hz, 1 H), 6.93 (dd, J=8.1 Hz, J'=8.7 Hz, 1H), 7.25–7.37 (m, 4H), 7.69 (d, J=6.6 Hz, 1H), 8.24 (bs, 2H), 8'46 (t, J=5.7 Hz, 1H) . $^{13}$C NMR (DMSO-d$_6$) 30.5, 31.4, 41.9, 42.3, 115.8, 118.9, 122.2, 124.5, 126.4, 126.9, 127.1, 127.2, 127.6, 128.6, 133.9,, 140.2, 147.8, 171.1, 171.4. MS (ESI) m/z 328.1 (MH$^+$).

Amide Phenol (4e) $^1$H NMR (DMSO-d$_6$) 2.17 (s, 3H), 2.52 (t, J=7.1 Hz, 2H), 2.65 (t, J=7.1 Hz, 2H), 4.01 (dt, J=5.1 Hz, J'=5.7 Hz, 2H), 4.28 (d, J=5.7 Hz, 2H), 6.74 (s, 2H), 7.26–7.37 (m, 4H), 7.51 (s, 1H), 8.27 (bs, 3H), 8.47 (t, J=5.7 Hz, 1H), 9.26 (s, 1H). $^{13}$C NMR (DMSO-d$_6$) 620.4, 30.5, 31.4, 41.7, 42.3, 115.7, 122.6, 124.9, 126.0, 127.1, 127.2, 127.4, 127.6, 128.6, 134.0, 140.2, 145.5, 171.0, 171.4. MS (ESI) m/z 342.1 (MH$^+$).

Amide Phenol (4f) $^1$H NMR (DMSO-d$_6$) 1.23 (s, 9H), 2.52 (t, J=6.7 Hz, 2H), 2.68 (t, J=6.7 Hz, 2H), 4.01 (dt, J=5.4 Hz, J'=5.7 Hz, 2H), 4.29 (d, J=5.7 Hz, 2H), 6.78 (d, J=8.7 Hz, 1H), 6.98 (d, J=8.7 Hz, 1H), 7.27–7.37 Im, 4H), 7.69 (s, 1H), 8.27 (bs, 3H), 8.48 (t, J=5.9 Hz, 1H), 9.41 (s, 1H). $^{13}$C NMR (DMSO-d$_6$) 30.5, 31.2, 31.4, 33.8, 41.9, 42.3, 115.8, 119.2, 121.5, 125.7, 127.1, 127.2, 127.6, 128.6, 134.0, 140.2, 141.3, 145.6, 171.3, 171.6. MS (ESI) m/z 384.2 (MH$^+$).

Benzoxazole (5a) $^1$H NMR (DMSO-d$_6$) 4.01 (dt, J=5.1 Hz, J'=6.0 Hz, 2H), 4.16 (s, 2H), 4.32 (d, J=6.3 Hz, 2H), 4.90 (s, 2H), 7.27–7.44 (m, 7H), 7.73 (d, J=8.1 Hz, 1H), 8.25 (bs, 2H), 8.53 (t, J=6.0 Hz, 1H). $^{13}$C NMR (DMSO-d$_6$) 41.6, 42.3, 66.9, 70.3, 115.3, 119.0, 121.6, 124.8, 125.5, 127.3, 127.6, 128.7, 134.0, 139.9, 147.6, 167.3, 168.8. High-resolution mass spectrum calcd for (C$_{18}$H$_{19}$N$_3$O$_3$+H)$^+$ m/z 326.1509, found 326.1517.

Benzoxazole (5b) $^1$H NMR (DMSO-d$_6$) 2.42 (s, 3H), 4.01 (dt, J=4.5 Hz, J'=6.0 Hz, 2H), 4.14 (s, 2H), 4.32 (d, J=6.0 Hz, 2H), 4.87 (s, 2H), 7.22–7.36(m, 6H), 7.55 (s, 1H), 8.25 (bs, 3H) , 8.52 (t, J=6.3 Hz, 1H) . $^{13}$C NMR (DMSO-d$_6$) 20.9, 41.6, 42.3, 65.1, 69.9, 110.4, 119.7, 126.5, 127.2, 127.5, 127.7, 128.3, 128.7, 134.1, 139.9, 145.3, 148.5, 162.5, 168.5. High-resolution mass spectrum calcd for (C$_{18}$H$_{21}$N$_3$O$_3$+H)$^+$ m/z 340.1661, found 340.1674.

Benzoxazole (5c) $^1$H NMR (DMSO-d$_6$) 1.34 (s, 9H), 4.01 {dt, J=4.5 Hz, J'=6.0 Hz, 2H), 4.15 (s, 2H), 4.33 (d, J=6.0 Hz, 2H), 4.88 (s, 2H), 7.26–7.37 (m, 4H), 7.49 (d, J=8.7 Hz, 1H), 7.63 (d, J=8.7 Hz, 1H), 8.26 (bs, 2H), 8.52 (t, J=6.3 Hz, 1H) . $^{13}$C NMR (DMSO-d$_6$) 31.4, 33.8, 41.6, 42.3, 65.4, 70.3, 110.5, 124.8, 127.3, 127.7, 128.7, 134.0, 139.9, 141.3, 145.5, 167.4, 168.8. High-resolution mass spectrum calcd for (C$_{22}$H$_{27}$N$_3$O$_3$+H)$^+$ m/z 382.2130, found 382.2122.

Benzoxazole (5d) $^1$H NMR (DMSO-d$_6$) 2.78 (t, J=7.2 Hz, 2H), 3.20 (t, J=7.2 Hz, 2H), 4.02 (dt, J=4.5 Hz, J'-5.7 Hz, 2H), 4.29 (d, J=5.4 Hz, 2H), 7.25–7.34 (m, 7H), 7.65 (d, J=7.7 Hz, 1H), 8.25 (bs, 2H), 8.60 (t, J=5.4 Hz, 1H). $^{13}$C NMR (DMSO-d$_6$) 28.2, 31.4, 41.9, 42.2, 110.5, 119.2, 124.2, 124.6, 127.1, 127.6, 128.6, 128.8, 133.9, 140.1, 150.2, 166.5, 170.5. MS (ESI) m/z 310.1 (MH$^+$).

Benzoxazole (5e) $^1$H NMR (DMSO-d$_6$) 2.41 (s, 3H), 2.77 (t, J=7.2 Hz, 2H), 3.17 (t, J=7.2 Hz, 2H), 4.01 (dt, J=5.1 Hz, J'=5.7 Hz, 2H), 4.30 (d, J=5.7 Hz, 2H), 7.15 (d, J=8.1 Hz, 1H), 7.27–7.38 (m, 4H), 7.46 (s, 1H), 7.51 (d, J=8.1 Hz, 1H), 8.32 (bs, 2H), 8.61 (t, J=6.0 Hz, 1H). $^{13}$C NMR (DMSO-d$_6$) 20.96, 28.2, 31.4, 41.9, 42.3, 109.9, 119.0, 125.5, 127.1, 127.6, 127.8, 128.3, 128.6, 128.8, 133.9, 140.0, 148.5, 166.5, 170.5. MS (ESI) m/z 324.1 (MH$^+$).

Benzoxazole (5f) $^1$H NMR (DMSO-d$_6$) 2.77 (t, J=7.2 Hz, 2H), 3.18 (t, J=7.2 Hz, 2H), 4.01 (dt, J=4.5 Hz, J'=6.0 Hz, 2H), 4.29 (d, J=5.7 Hz, 2H), 7.24–7.37 (m, 5H), 7.52 (d, J=8.1 Hz, 1H), 7.64 (s, 1H), 8.28 (bs, 2H), 8.60 (t, J=5.4 Hz, 1H). $^{13}$C NMR (DMSO-d$_6$) 28.2, 31.2, 31.6, 34.6, 41.9, 42.6, 109.6, 115.6, 119.2, 120.8, 122.1, 125.7, 127.1,127.6, 128.8, 134.0, 140.1, 145.6, 166.5, 170.5. MS (ESI) m/z 366.2 (MH$^+$).

Synthesis of Solid Phase Libraries

Solid phase split pool techniques were applied to the general synthetic techniques described above to afford combinatorial library represented in the tables which follow. The general structure represented by each library is shown at the top of each table.

A mixture of ten diamines, as shown in Table 1, were coupled to a hydroxyl bearing resin and split into 10 portions. Each portion was independently reacted with one of diacid 1–10 (of Table 1). The resultant products were each split into eight portions. Each of these eight portions was then reacted with one of aminophenols, A–H (of Table 1). The resultant products were cyclized and dehydrated according to the method described above. Hydrolysis for the resin afforded benzoxazoles which were tested, for activity, the results of which are represented in Tables 1a–1g.

TABLE 1

TABLE 1-continued

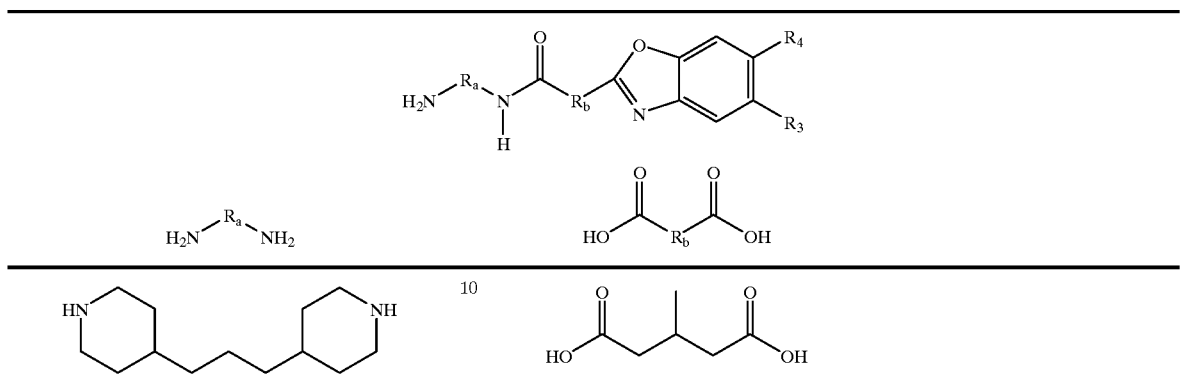

TABLE 1a

Modified Kirby-Bauer Assay Against *E. Coli*

|   | 1 | 2 | 3 | 4 | 5 | 6 | 7 | 8 | 9 | 10 |
|---|---|---|---|---|---|---|---|---|---|----|
| A | 0 | 0 | 0 | 0 | 0 | 0 | 0 | 8 | 0 | 0 |
| B | 0 | 0 | 0 | 0 | 8 | 0 | 0 | 8 | 0 | 0 |
| C | 8 | 8 | 8 | 8 | 8 | 8 | 8 | 8 | 8 | 8 |
| D | 9 | 10 | 9 | 9 | 10 | 10 | 9 | 9 | 10 | 9 |
| E | 0 | 0 | 0 | 0 | 0 | 0 | 0 | 8 | 0 | 0 |
| F | 0 | 0 | 0 | 0 | 0 | 8 | 0 | 8 | 8 | 0 |
| G | 0 | 0 | 0 | 0 | 0 | 0 | 0 | 0 | 0 | 0 |
| H | 0 | 0 | 0 | 0 | 0 | 0 | 0 | 0 | 0 | 0 |

Tabulated results show zone size of inhibited microbial growth (diameter in mm (millimeters)). DMSO and Tetracylcine (10 mg/ml) were used as controls and showed 0 and 22 mm of inhibition respectively. Results indicate that compounds within libraries have low activity against *E. coli* growth as shown by the modified Kirby-Bauer assay.

TABLE 1b

Modified Kirby-Bauer Assay Against *Candida*

|   | 1 | 2 | 3 | 4 | 5 | 6 | 7 | 8 | 9 | 10 |
|---|---|---|---|---|---|---|---|---|---|----|
| A | 9 | 0 | 0 | 0 | 0 | 0 | 9 | 9 | 0 | 0 |
| B | 9 | 0 | 0 | 0 | 0 | 0 | 9 | 9 | 0 | 0 |
| C | 9 | 9 | 9 | 9 | 9 | 9 | 9 | 9 | 9 | 9 |
| D | 9 | 9 | 9 | 9 | 9 | 9 | 9 | 9 | 9 | 9 |
| E | 0 | 0 | 0 | 0 | 0 | 0 | 9 | 9 | 9 | 0 |
| F | 0 | 0 | 0 | 0 | 0 | 0 | 9 | 9 | 9 | 0 |
| G | 0 | 0 | 0 | 0 | 0 | 0 | 9 | 0 | 0 | 0 |
| H | 0 | 0 | 0 | 0 | 0 | 0 | 0 | 0 | 0 | 0 |

Tabulated results show zone size of inhibited microbial growth (diameter in mm (millimeters)). DMSO, (+) cis-itraconazole and (−) cis itraconazole (10 mg/ml) were used as controls and showed 0 , 12 and 15 mm of inhibition respectively. Results indicate that compounds within libraries have low activity against Candida growth as shown by the modified Kirby-Bauer assay.

TABLE 1c

Modified Kirby-Bauer Assay Against *Saccharomyces*

|   | 1 | 2 | 3 | 4 | 5 | 6 | 7 | 8 | 9 | 10 |
|---|---|---|---|---|---|---|---|---|---|----|
| A | 9 | 0 | 0 | 0 | 9 | 0 | 9 | 9 | 0 | 0 |
| B | 9 | 0 | 0 | 0 | 9 | 0 | 9 | 9 | 0 | 0 |

TABLE 1c-continued

Modified Kirby-Bauer Assay Against *Saccharomyces*

|   | 1 | 2 | 3 | 4 | 5 | 6 | 7 | 8 | 9 | 10 |
|---|---|---|---|---|---|---|---|---|---|----|
| C | 9 | 9 | 9 | 9 | 9 | 9 | 9 | 9 | 9 | 9 |
| D | 9 | 9 | 9 | 9 | 9 | 9 | 9 | 9 | 9 | 9 |
| E | 0 | 0 | 0 | 0 | 0 | 0 | 9 | 9 | 0 | 0 |
| F | 0 | 0 | 0 | 0 | 0 | 0 | 9 | 9 | 0 | 0 |
| G | 0 | 0 | 0 | 0 | 0 | 0 | 0 | 0 | 0 | 0 |
| H | 0 | 0 | 0 | 0 | 0 | 0 | 0 | 0 | 0 | 0 |

Tabulated results show zone size of inhibited microbial growth (diameter in mm (millimeters)). DMSO, (+) cis-itraconazole and (−) cis itraconazole (10 mg/ml) were used as controls and showed 0 , 12 and 15 mm of inhibition respectively. Results indicate that compounds within libraries have low activity against Saccharomyces growth as shown by the modified Kirby-Bauer assay.

TABLE 1d

Modified Kirby-Bauer Assay Against *Staphylococcusaureus*

|   | 1 | 2 | 3 | 4 | 5 | 6 | 7 | 8 | 9 | 10 |
|---|---|---|---|---|---|---|---|---|---|----|
| A | 13 | 0 | 10 | 0 | 0 | 10 | 9 | 12 | 0 | 0 |
| B | 11 | 0 | 10 | 0 | 0 | 10 | 9 | 14 | 10 | 9 |
| C | 13 | 11 | 11 | 10 | 11 | 12 | 10 | 15 | 13 | 11 |
| D | 14 | 20 | 14 | 13 | 12 | 16 | 11 | 17 | 14 | 13 |
| E | 9 |   | 0 | 0 | 0 | 0 | 8 | 11 | 12 | 0 |
| F | 13 | 15 | 11 | 9 | 8 | 15 | 11 | 17 | 14 | 9 |
| G | 0 | 0 | 0 | 0 | 8 | 8 | 8 | 8 | 10 | 0 |
| H | 0 | 0 | 0 | 0 | 0 | 0 | 0 | 11 | 0 | 0 |

Tabulated results show zone size of inhibited microbial growth (diameter in mm (millimeters)). DMSO and Tetracylcine (10 mg/ml) were used as controls and showed 0 and 25 mm of inhibition respectively. Results indicate that compounds within libraries have low activity against Staphylococcus aureus growth as shown by the modified Kirby-Bauer assay.

It will be appreciated that the results of Kirby-Bauer testing and determination of the inhibition do not always correlate perfectly, due to differences in compound solubility and the like. It will also be appreciated that compounds which show little activity in the in vitro assays described herein can have in vivo anti-microbial activity. Without wishing to be bound by any theory, it is believed that other assays not tested are more predictive of in vivo activity than is the Kirby-Bauer screening.

TABLE 1e

HNE Inhibition

|   | 1 | 2 | 3 | 4 | 5 | 6 | 7 | 8 | 9 | 10 |
|---|---|---|---|---|---|---|---|---|---|---|
| A | 14.79 | 41.65 | 35.14 | 35.91 | 34.78 | 33.32 | 39.35 | 45.35 | 38.68 | 33.83 |
| B | 20.32 | 31.85 | 37.47 | 37.40 | 38.95 | 34.68 | 41.10 | 51.34 | 33.62 | 37.78 |
| C | 14.08 | 11.12 | 18.96 | 39.85 | 40.86 | 35.72 | 38.44 | 54.98 | 38.10 | 36.71 |
| D | 25.20 | 26.15 | 16.64 | 27.48 | 16.83 | 25.49 | 25.68 | 5.381 | 5.409 | 6.836 |
| E | 16.55 | 23.50 | 19.44 | 25.75 | 30.40 | 12.70 | 21.73 | 14.14 | 31.33 | 30.24 |
| F | 38.15 | 24.75 | 29.36 | 29.96 | 33.15 | 36.63 | 35.61 | 29.27 | 30.36 | 35.99 |
| G | 31.09 | 27.15 | 27.19 | 29.35 | 24.10 | 21.31 | 28.57 | 25.68 | 33.46 | 31.80 |
| H | 35.85 | 33.88 | 32.24 | 35.15 | 36.48 | 34.82 | 27.79 | 35.70 | 30.74 | 35.56 |

Results indicate that certain compounds in the library inhibit activity of human neutrophil elastase. The values represent relative activity of the enzyme in the presence of the compounds. Lower values indicate that the enzyme is inhibited by the compounds.

TABLE 1f

HNE Inhibition
Certain compounds were selected and their $IC_{50}$'s were measured and are shown in the Table below.

| Compound | I | V | $V_0$ | $IC_{50}$ |
|---|---|---|---|---|
| FW | μM |  |  | μM |
| C2 | 60 | 17.96 | 36.42 | 58.4 |
| D8 | 60 | 9.16 | 36.42 | 20.2 |
| D9 | 60 | 19.75 | 36.42 | 71.1 |

TABLE 1f-continued

HNE Inhibition
Certain compounds were selected and their $IC_{50}$'s were measured and are shown in the Table below.

| Compound | I | V | $V_0$ | $IC_{50}$ |
|---|---|---|---|---|
| D10 | 60 | 23.15 | 36.42 | 105 |
| E6 | 600 | 10.46 | 36.42 | 242 |

$IC_{50}$ of Potential Elastase Inhibitors
$V_0$=rate of enzyme reaction
V=rate of enzyme reaction in the presence of the inhibitor
I=concentration of the inhibitor $$IC_{50} = \frac{[I]V}{(V_o - V)}$$

TABLE 1g

5 HT$_2$ Antagonism

|   | 1 | 2 | 3 | 4 | 5 | 6 | 7 | 8 | 9 | 10 |
|---|---|---|---|---|---|---|---|---|---|---|
| A | 0.282 | 0.242 | 0.278 | 0.197 | 0.17 | 0.279 | 0.317 | 0.168 | 0.193 | 0.246 |
| B | 0.262 | 0.226 | 0.258 | 0.385 | 0.317 | 0.289 | 0.378 | 0.18 | 0.267 | 0.351 |
| C | 0.177 | 0.352 | 0.19 | 0.277 | 0.178 | 0.259 | 0.277 | 0.303 | 0.398 | 0.211 |
| D | 0.309 | 0.286 | 0.273 | 0.165 | 0.676 | 0.451 | 0.507 | 0.097 | 0.471 | 0.411 |
| E | 0.246 | 0.256 | 0.339 | 0.273 | 0.265 | 0.317 | 0.212 | 0.253 | 0.217 | 0.211 |
| F | 0.221 | 0.277 | 0.316 | 0.133 | 0.156 | 0.277 | 0.252 | 0.171 | 0.244 | 0.262 |
| G | 0.201 | 0.192 | 0.141 | 0.205 | 0.186 | 0.175 | 0.181 | 0.158 | 0.344 | 0.23 |
| H | 0.147 | 0.27 | 0.17 | 0.17 | 0.228 | 0.272 | 0.228 | 0.199 | 0.259 | 0.174 |

Results indicate that certain compounds in the library antagonize 5-HT$_2$ receptors. The values represent relative activity of the substrate in the presence of the compounds. Values greater than 0.25 indicate that the compound acts as an antagonist toward R HT$_2$ receptors.

Libraries in Tables 2–7 were prepared by reaction of a hydroxyl bearing resin with carbonyl diimidazole (CDI) to form an activated support. The activated support was reacted with a combination of five diamines. The mixture was then split into ten equivalent portions and each portion was reacted with a single amino acid (designated #1–10 of the libraries, Tables 2–7), to form a mixture of amides. Each mixture was further reacted with a 4-(N-Fmoc)-amino-3-hydroxy benzoic, (designated A–H of the libraries, Tables 2–7), the amine protecting group was removed and the corresponding 3-hydroxy-4-amide groups were cyclized and dehydrated with triphenyl phosphine and diethylazodicarboxylate, affording a mixture of benzoxazoles retained on the polymer support. Cleavage of the mixture afforded soluble libraries of benzoxazoles.
TABLE 2
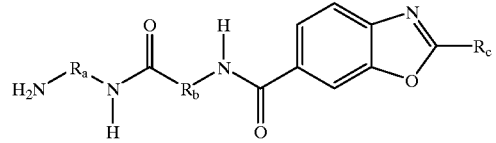
| | $R_b$ $H_2N$—COOH | | $R_c$—COOH | $H_2N$—$R_a$—$NH_2$ |
|---|---|---|---|---|
| 1 | 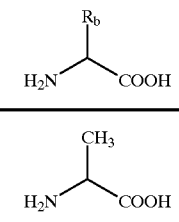 | A | 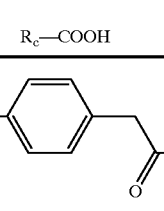 | 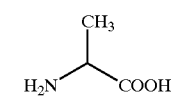 |
| 2 | 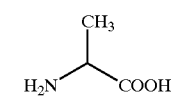 | B | 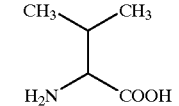 | 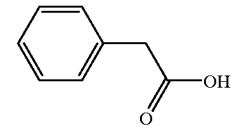 |
| 3 | 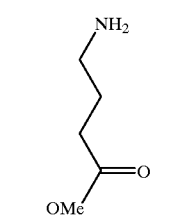 | C | 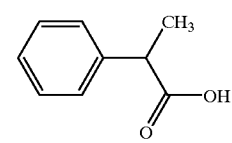 | 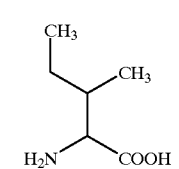 |
| 4 | 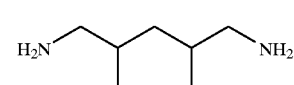 | D | 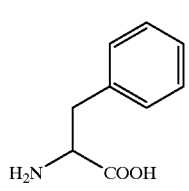 | 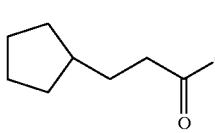 |
| 5 | 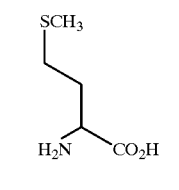 | E | 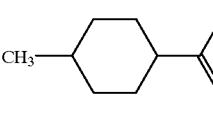 | 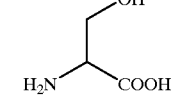 |
| 6 | 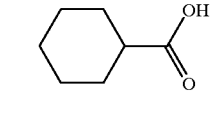 | F | | |
| 7 | | G | | |

TABLE 2-continued
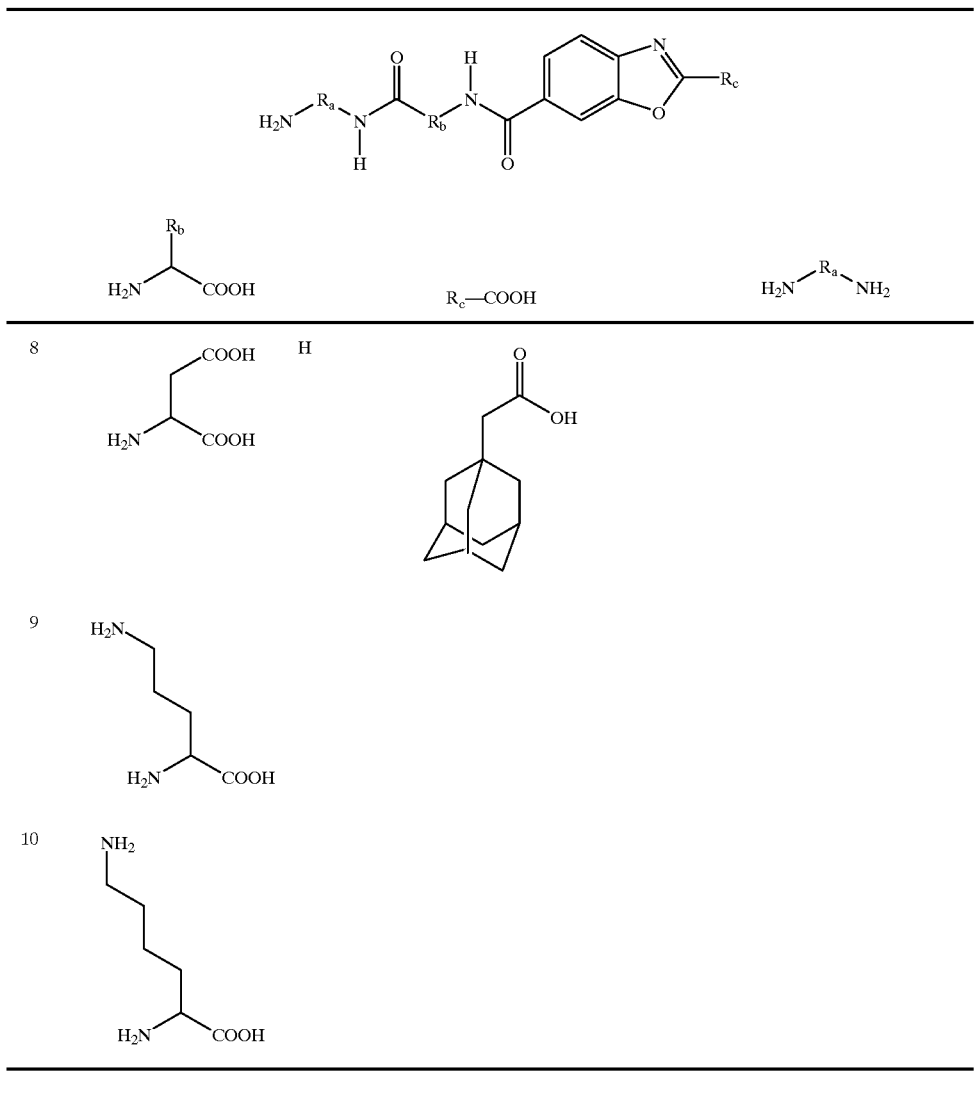
TABLE 3
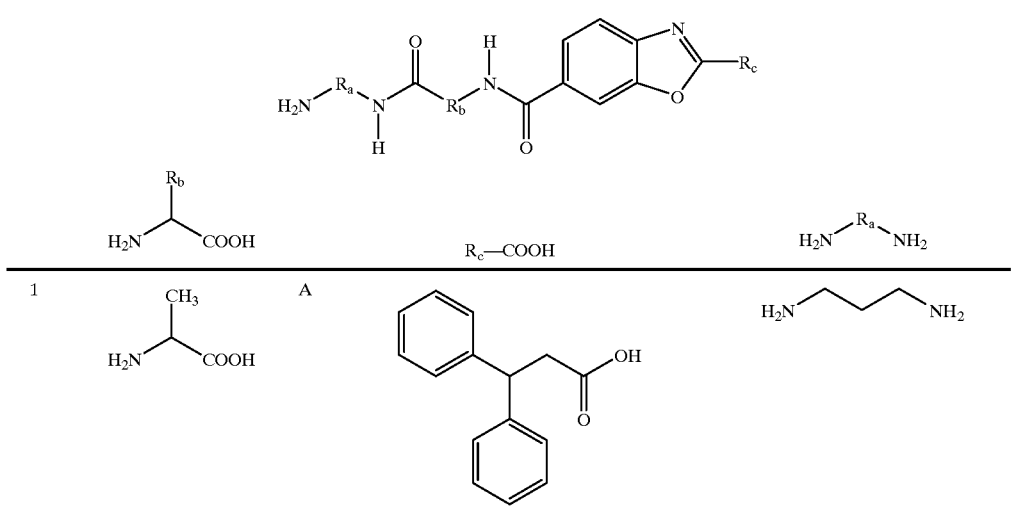

TABLE 3-continued

| # | R_b (H2N-Rb-COOH) | | R_c (Rc-COOH) | R_a (H2N-Ra-NH2) |
|---|---|---|---|---|
| 2 | Valine | B | 4-biphenylacetic acid | piperazine |
| 3 | 4-amino-methyl ester ketone | C | 2-thiopheneacetic acid | 1,2-diaminocyclohexane |
| 4 | Isoleucine | D | 1-naphthaleneacetic acid | 1,3-bis(aminomethyl)benzene |
| 5 | Phenylalanine | E | 3,4,5-trimethoxyphenylacetic acid | 1,3-bis(aminomethyl)cyclohexane |
| 6 | Methionine | F | 2-methylindole-3-acetic acid | |
| 7 | Serine | G | 2-fluorophenylacetic acid | |
| 8 | Aspartic acid | H | 3-pyridylacetic acid | |

TABLE 3-continued

| | $R_b$ $H_2N$-CH-COOH | $R_c$—COOH | $H_2N$-$R_a$-$NH_2$ |
|---|---|---|---|
| 9 | H₂N-(CH₂)₃-CH(NH₂)-COOH (ornithine) | | |
| 10 | H₂N-(CH₂)₄-CH(NH₂)-COOH (lysine) | | |

TABLE 4

| | $R_b$ $H_2N$-CH-COOH | | $R_c$—COOH | $H_2N$-$R_a$-$NH_2$ |
|---|---|---|---|---|
| 1 | Ala (CH₃) | A | phenoxyacetic acid | $H_2N$-(CH₂)₃-$NH_2$ |
| 2 | Val | B | 2-methylcyclopropanecarboxylic acid | homopiperazine (HN⌒NH) |
| 3 | Ile | C | cyclopropanecarboxylic acid | $H_2N(CH_2)_2O$—$(CH_2)_2O$—$(CH_2)_2$—$NH_2$ |

TABLE 4-continued
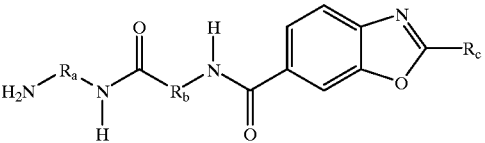
| | $R_b$<br>$H_2N$-CH-COOH | | $R_c$—COOH | $H_2N$-$R_a$-$NH_2$ |
|---|---|---|---|---|
| 4 | 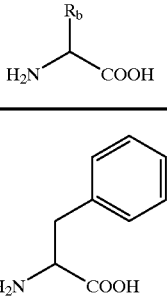 | D | 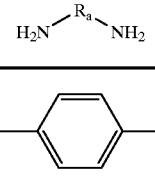 | 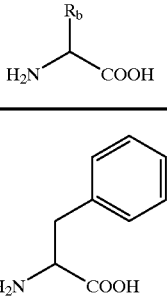 |
| 5 | 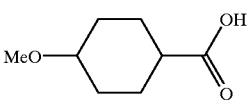 | E | 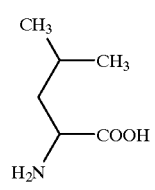 | 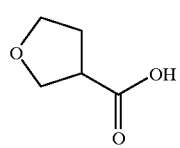 |
| 6 | 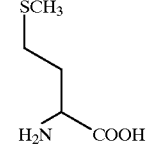 | F | 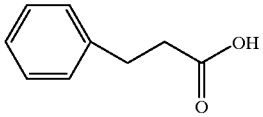 | |
| 7 | 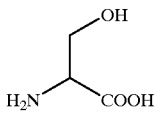 | G | 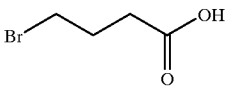 | |
| 8 | 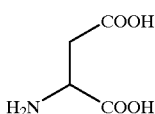 | H | 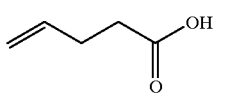 | |
| 9 | 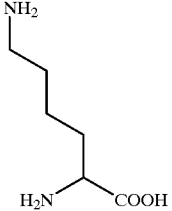 | | | |
| 10 | 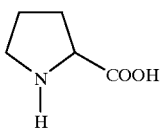 | | | |

TABLE 5

(structure shown: H₂N-Ra-NH-C(=O)-Rb-NH-C(=O)-[benzoxazole]-Rc)

| | Rb (H₂N-CH(Rb)-COOH) | | Rc—COOH | H₂N-Ra-NH₂ |
|---|---|---|---|---|
| 1 | Ala (CH₃) | A | Ala (CH₃) | H₂N-(CH₂)₃-NH₂ |
| 2 | Val | B | Val | homopiperazine (HN-7-membered ring-NH) |
| 3 | Ile | C | Ile | H₂(CH₂)₂O—(CH₂)₂O—(CH₂)₂—NH₂ |
| 4 | Phe | D | Phe | H₂N-CH₂-C₆H₄-CH₂-NH₂ (para) |
| 5 | Leu | E | Leu | bis(4-amino-3-methylcyclohexyl)methane |
| 6 | Met (SCH₃) | F | Met (SCH₃) | |
| 7 | Ser (OH) | G | Ser (OH) | |
| 8 | Asp (COOH) | H | Lys (H₂N-(CH₂)₄-CH(NH₂)COOH) | |

TABLE 5-continued (structure: H2N-Ra-N(H)-C(O)-N(H)-Rb-C(O)-N(H)-benzoxazole-Rc)

| Rb-CH(NH2)-COOH | Rc—COOH | H2N-Ra-NH2 |

9: H2N-(CH2)4-CH(NH2)-COOH (lysine)

10: proline

TABLE 6

(structure: H2N-Ra-N(H)-C(O)-N(H)-Rb-C(O)-N(H)-benzoxazole-Rc)

| # | Rb-CH(NH2)-COOH | | Rc—COOH | H2N-Ra-NH2 |
|---|---|---|---|---|
| 1 | alanine (CH3) | A | 3-methoxyphenylacetic acid | H2N-(CH2)3-NH2 |
| 2 | valine ((CH3)2CH) | B | 2-methylphenylacetic acid | homopiperazine (HN-(CH2)3-NH ring) |
| 3 | isoleucine (CH(CH3)CH2CH3) | C | 4-methylphenylacetic acid | H2N(CH2)2O—(CH2)2O—(CH2)2—NH2 |

TABLE 6-continued
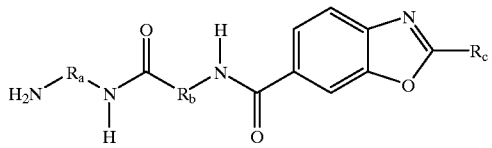
| | $R_b$<br>$H_2N$—COOH | | $R_c$—COOH | $H_2N$—$R_a$—$NH_2$ |
|---|---|---|---|---|
| 4 | 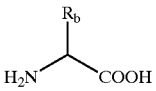 | D |  | 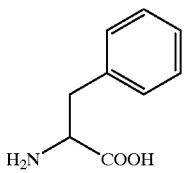 |
| 5 | 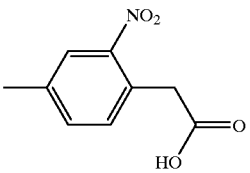 | E | 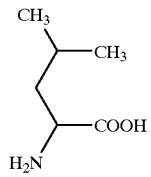 | 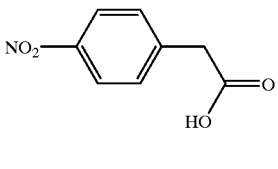 |
| 6 | 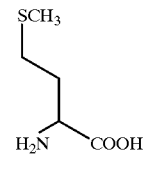 | F | 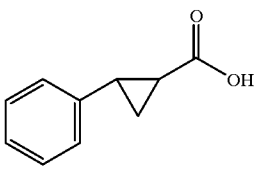 | |
| 7 | 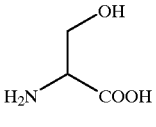 | G | 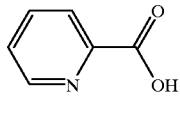 | |
| 8 | 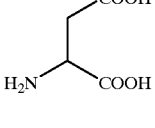 | H | 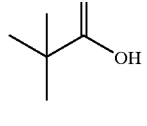 | |
| 9 | 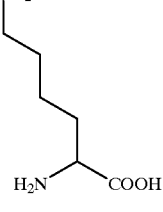 | | | |
| 10 | 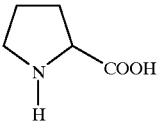 | | | |

TABLE 7

(structural diagram of scaffold with H₂N-Rₐ-N(H)-C(O)-Rᵦ-N(H)-C(O)-benzoxazole-Rc)

| | Rᵦ (H₂N-CH-COOH) | | Rc—COOH | | H₂N-Rₐ-NH₂ |
|---|---|---|---|---|---|
| 1 | alanine (CH₃) | A | 4-(trifluoromethyl)phenylacetic acid | | 1,3-diaminopropane |
| 2 | valine | B | 3-cyclohexylpropanoic acid | | piperazine |
| 3 | isoleucine | C | 3-methoxycyclohexanecarboxylic acid | | 1,2-diaminocyclohexane |
| 4 | phenylalanine | D | 3-methoxycyclohexanecarboxylic acid | | 1,3-bis(aminomethyl)benzene |
| 5 | leucine | E | 2-methylcyclohexanecarboxylic acid | | 1,3-bis(aminomethyl)cyclohexane |
| 6 | methionine | F | 5-bromopentanoic acid | | |
| 7 | 2-methylcyclopropanecarboxylic acid | G | 2-(trifluoromethyl)phenylacetic acid | | |
| 8 | isoleucine | H | 3-methylcyclohexanecarboxylic acid | | |

TABLE 7-continued

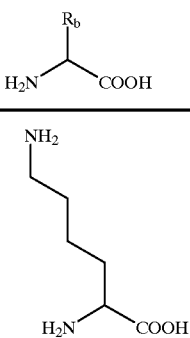

9 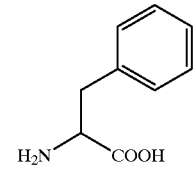

10 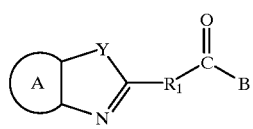

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A compound represented by the formula (Formula V):

(V)

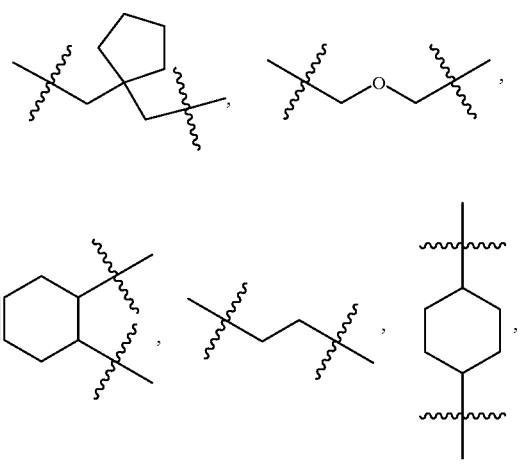

wherein:

A is a substituted or unsubstituted aryl group;

Y is O or S;

$R_1$ is a linear or branched, substituted or unsubstituted alkyl group, a substituted or unsubstituted alkenyl group, an alkoxyalkyl group, a thioalkoxyalkyl group, or a substituted or unsubstituted aryl group; and B is —$N(R_2)R_3N(R_4)(R_5)$, wherein $R_2$ is hydrogen atom, $R_3$ is a linear or branched, substituted or unsubstituted alkyl diradical; and $R_4$ and $R_5$ are each independently a hydrogen atom, a group covalently or non-covalently bonded to a solid support, or $R_2$ and $R_4$ taken together represent a substituted or unsubstituted cycloalkyl group.

2. The compound of claim 1, wherein $R_3$ is an alkyl diradical.

3. The compound of claim 1, wherein A is a substituted aryl group.

4. The compound of claim 3, wherein said substituted aryl group includes one or more substituents, wherein each substituent is either $CH_3$—, $(CH_3)_3C$—, $C_6H_5$—, $CH_3CH_2SO_2$—, Cl—, or $NO_2$—.

5. The compound of claim 3, wherein said substituted aryl group includes a substituent located para to Y in Formula V.

6. The compound of claim 1, wherein $R_1$ and $R_3$ are either —$CH_2CH_2CH_2$— or —$CH_2CH_2$—.

7. The compound of claim 1, wherein $R_1$ is an alkyl group, an alkoxyalky group, an alkenyl group, or a thioalkoxyalkyl which is selected from -continued

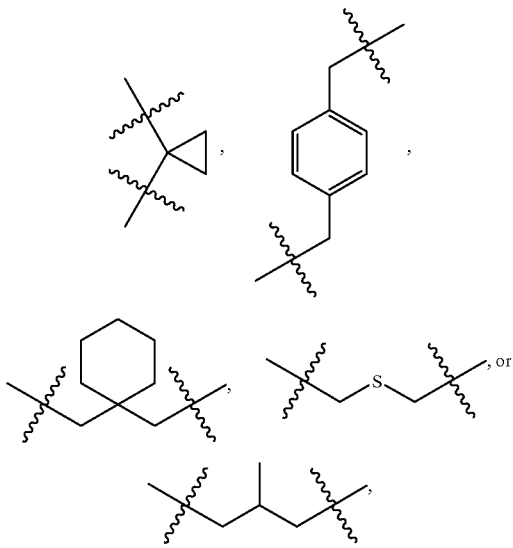

8. The compound of claim 1, wherein B is

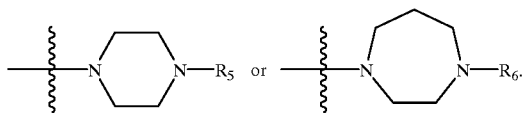

9. The compound of claim 1, wherein said linker is a diamine.

10. The compound of claim 9, wherein said solid support is selected from the group consisting of silica, silicon, glass, polystyrene, polystyrene/divinylbenzene copolymer, polyacrylamide, Tenta-gel, Wang resin, Rapp resin, Merrifield resin, and Rink resin.

11. A compound represented by the formula (Formula VI):

(V)

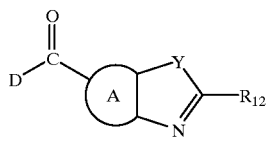

wherein:
A is an aryl group;
Y is O or S;
D is

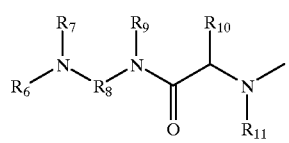

wherein
$R_6$ and $R_7$ are each independently a hydrogen atom, or a group covalently or non-covalently bonded to a solid support;
$R_8$ is a linear or branched, substituted or unsubstituted alkyl group, an alkoxyalkyl group, or a substituted or unsubstituted aryl group;
$R_9$ is a hydrogen atom or $R_7$ and $R_9$ when taken together represent a cycloalkyl group;
$R_{10}$ is a linear or branched, substituted or unsubstituted alkyl group or substituted or unsubstituted aryl group;
$R_{11}$ is a hydrogen atom; and
$R_{12}$ is a linear or branched, substituted or unsubstituted alkyl group, linear or branched, substituted or unsubstituted alkenyl group, or a substituted or unsubstituted aryl group; or a salt thereof.

12. The compound of claim 11, wherein $R_8$ is an alkyl group.

13. The compound of claim 12, wherein $R_8$ is an alkyl group or an alkoxyalkyl group which is

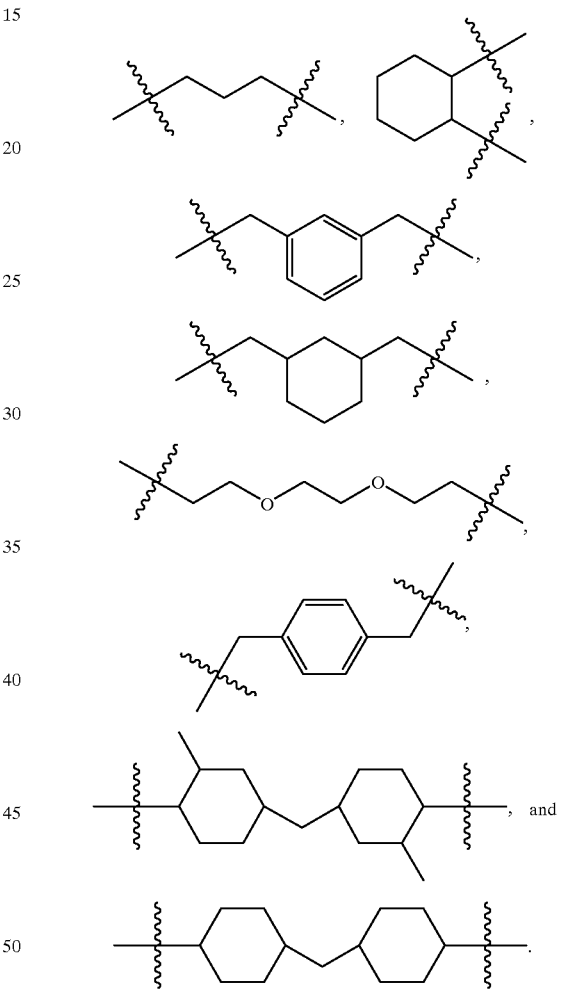

14. The compound of claim 11, wherein D is

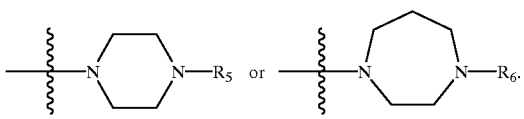

15. The compound of claim 11, wherein $R_{10}$ is a methyl, iso-propyl, butyl, toluyl, methyl-2-thioethyl, methylol, acetate, 3-aminopropyl, 4-aminobutyl, 2-methylpropyl, or a prolinyl group.

16. The compound of claim 12, wherein $R_{12}$ is a p-methoxy-toluyl, toluyl, 2-ethylbenzyl, 3-methylpyridyl, 2-cyclopentylethyl, 4-methylcyclohexyl, cyclohexyl, 1-methyladamantyl, 2,2-diphenylethyl, p-phenyl-toluyl, 2-methylthiophenyl, alpha-methylnaphthalenyl, 3,4,5-trimethoxytoluyl, 2-methyl-3-methyl-indolyl, 2-fluorotoluyl, 4-methylpyridinyl, anisolyl, cyclopropyl, 2-methylcyclopropyl, 4-methoxycyclohexyl, tetrahydrofuryl, ethylbenzene, 3-bromopropyl, 1-butenyl, methyl, iso-propyl, butyl, toluyl, methyl-2-thioethyl, methylol, acetate, 3-aminopropyl, 4-aminobutyl, 2-methylpropyl, propyl, 3-methoxytoluyl, ortho-xylyl, para-xylyl, ortho-nitrotoluyl, para-nitrotoluyl, phenylcyclopropyl, tert-butyl, para-trifluoromethanetoluyl, ethylcyclohexyl, 6-methoxymethanenaphthalenyl, 3-methoxycyclohexyl, 2-methylcyclohexyl, ortho-trifluoromethanetoluyl, or a 3-methylcyclohexyl group.

17. The compound of claim 12, wherein the group bonded to the solid support is a diamine.

18. The compound of claim 17, wherein said solid support is selected from the roup consisting of silica silicon, glass polystyrene, polystyrene/divinvlbenzene copolymer, polyacrylamide, Tenta-gel, Wang Resin, Rapp resin, Merrifield resin, and Rink resin.

19. A pharmaceutical composition comprising an effective amount of a compound represented by the formula (Formula V):

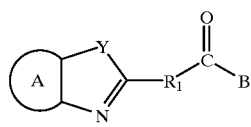
(V)

wherein:

A is a substituted or unsubstituted aryl group;

Y is O or S;

$R_1$ is a linear or branched, substituted or unsubstituted alkyl group, a substituted or unsubstituted alkenyl group, and alkoxyalkyl group, a thioalkoxyalkyl group, or a substituted or unsubstituted aryl group; and B is —$N(R_2)R_3N(R_4)(R_5)$, wherein $R_2$ is hydrogen atom; $R_3$ is a linear or branched, substituted or unsubstituted alkyl diradical; and $R_4$ and $R_5$ are each independently a hydrogen atom, a group covalently or non-covalently bonded to a solid support, or $R_2$ and $R_4$ taken together represent a substituted or unsubstituted cycloalkyl group.

20. The pharmaceutical composition of claim 19 further comprising a pharmaceutically-acceptable vehicle.

21. A pharmaceutical composition comprising an effective amount of a compound represented by the formula (Formula VI):

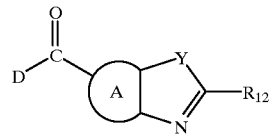
(V)

wherein:

A is an aryl group;

Y is O or S;

D is

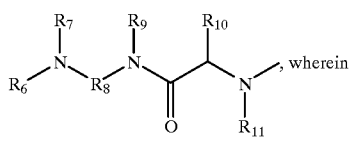
, wherein

, wherein $R_6$ and $R_7$ are each independently a hydrogen atom, or a group covalently or non-covalently bonded to a solid support $R_8$ is a linear or branched, substituted or unsubstituted alkyl group, an alkoxyalkyl group, or a substituted or unsubstituted aryl group;

$R_9$ is a hydrogen atom or $R_7$ and $R_9$ when taken together represent a cycloalkyl group;

$R_{10}$ is a linear or branched, substituted or unsubstituted alkyl group or substituted or unsubstituted aryl group;

$R_{11}$ is a hydrogen atom; and $R_{12}$ is a linear or branched, substituted or unsubstituted alkyl group, linear or branched, substituted or unsubstituted alkenyl group, or a substituted or unsubstituted aryl group; or a salt thereof.

22. The pharmaceutical composition of claim 21 further comprising a pharmaceutically-acceptable vehicle.

* * * * *